United States Patent
Reddy, Jr. et al.

(10) Patent No.: US 11,027,274 B2
(45) Date of Patent: Jun. 8, 2021

(54) MICROFLUIDIC CARTRIDGE AND STACKED TESTING ASSEMBLY WITH MICROFLUIDIC CARTRIDGE THEREOF

(71) Applicants: FOXCONN INTERCONNECT TECHNOLOGY LIMITED, Grand Cayman (KY); Prenosis, Inc., Champaign, IL (US)

(72) Inventors: Bobby Reddy, Jr., Urbana, IL (US); Rashid Bashir, Champaign, IL (US); Samuel Wachspress, Urbana, IL (US); Lauren Penrose, Mahomet, IL (US); Chun-Yi Chang, New Taipei (TW); Been-Yang Liaw, New Taipei (TW)

(73) Assignees: FOXCONN INTERCONNECT TECHNOLOGY LIMITED, Grand Cayman (KY); Prenosis, Inc.

( * ) Notice: Subject to any disclaimer, the term of this patent is extended or adjusted under 35 U.S.C. 154(b) by 326 days.

(21) Appl. No.: 15/880,504

(22) Filed: Jan. 25, 2018

(65) Prior Publication Data
US 2018/0214870 A1   Aug. 2, 2018

Related U.S. Application Data

(60) Provisional application No. 62/450,083, filed on Jan. 25, 2017.

(51) Int. Cl.
*B01L 3/00* (2006.01)
*G01N 33/543* (2006.01)

(52) U.S. Cl.
CPC ... *B01L 3/502707* (2013.01); *B01L 3/502761* (2013.01); *G01N 33/5438* (2013.01); *B01L 2200/025* (2013.01); *B01L 2200/027* (2013.01); *B01L 2200/028* (2013.01); *B01L 2200/0652* (2013.01); *B01L 2300/0645* (2013.01);
(Continued)

(58) Field of Classification Search
CPC ........ B01L 3/502707; B01L 3/502761; B01L 2300/0883; B01L 2400/086; B01L 2200/028; B01L 2200/025; B01L 2200/027; B01L 2300/0887; B01L 2300/0681; B01L 2200/0652; B01L 2300/0645; B01L 3/5027; G01N 33/5438; G01N 35/00
See application file for complete search history.

(56) References Cited

U.S. PATENT DOCUMENTS 8,171,778 B2   5/2012  Ayliffe
2003/0118481 A1*  6/2003  Briscoe ................. F28D 9/00
                                                 422/89

(Continued)

FOREIGN PATENT DOCUMENTS

| CN | 105164538 A | 12/2015 |
|---|---|---|
| TW | 201513337 A | 4/2015 |
| TW | 201604528 A | 2/2016 |

*Primary Examiner* — Samuel P Siefke
*Assistant Examiner* — Quocan B Vo
(74) *Attorney, Agent, or Firm* — Ming Chieh Chang; Wei Te Chung

(57) ABSTRACT

A stacked testing assembly (100) includes a microfluidic cartridge (10) for analyzing a fluid sample and a testing setup, said microfluidic cartridge includes a number of layers (1, 2) stacked in a height direction with many different kinds of combinations, said testing setup (20) is capable of assembling and testing all kinds of said layers combinations with no change to the setup.

1 Claim, 30 Drawing Sheets

(52) U.S. Cl.
CPC ............... *B01L 2300/0681* (2013.01); *B01L 2300/0883* (2013.01); *B01L 2300/0887* (2013.01); *B01L 2400/086* (2013.01)

(56) References Cited

U.S. PATENT DOCUMENTS

| | | | | |
|---|---|---|---|---|
| 2004/0043479 | A1* | 3/2004 | Briscoe | B01L 3/5025 |
| | | | | 435/288.5 |
| 2005/0284213 | A1* | 12/2005 | Karp | G01N 30/6026 |
| | | | | 73/61.52 |
| 2006/0160206 | A1* | 7/2006 | Holmquist | B01L 3/5027 |
| | | | | 435/287.2 |
| 2007/0072287 | A1* | 3/2007 | Morisette | C12M 23/28 |
| | | | | 435/287.2 |
| 2013/0295588 | A1 | 11/2013 | Watkins | |
| 2013/0323125 | A1* | 12/2013 | Deane | B01L 3/5027 |
| | | | | 422/73 |
| 2014/0038193 | A1* | 2/2014 | Spoto | B01L 3/5027 |
| | | | | 435/6.12 |
| 2015/0167052 | A1* | 6/2015 | Griffin | B01L 3/502715 |
| | | | | 435/6.12 |
| 2016/0369323 | A1* | 12/2016 | Revilla | B01L 3/5027 |
| 2017/0292104 | A1* | 10/2017 | Ebrahimi Warkiani | |
| | | | | C12M 29/10 |
| 2020/0071727 | A1* | 3/2020 | Tandon | B01L 3/50273 |

* cited by examiner

MICROFLUIDIC CARTRIDGE AND STACKED TESTING ASSEMBLY WITH MICROFLUIDIC CARTRIDGE THEREOF

BACKGROUND OF THE INVENTION

1. Field of the Invention

The present invention relates to a microfluidic cartridge comprised of many independent layers for measuring quantities from a fluid sample and an accompanying testing/chemical modification assembly capable of testing individual layers or combinations of layers that make up the cartridge design.

2. Description of Related Art

Microfluidic chips have received much attention over the past 2 decades for the potential use in many applications. These devices, where small volumes of fluids are manipulated through micro-channel networks that have been molded or patterned, can be used for research applications and point of care diagnostics. Microfluidic technology can enable point of care diagnostics, which can perform measurements from patient samples at much more convenient locations. Because of the use of small volumes of fluids, these devices can decrease sample consumption. In addition, such devices can automate many sample preparation processes typically performed at the benchtop with a technician, enabling much more convenient use in diagnostic situations. To date, most microfluidic designs are very specialized with very little commonality across platforms or even a single cartridge design. This lack of standardization has enforced the need for each new microfluidic device company to formulate designs, build manufacturing processes, quality control tests, etc. completely from scratch. The field of microfluidic devices could greatly benefit from an industry standard of design rules. Once these design rules are established, multiple companies and manufacturers could benefit from the commonality between designs.

In this disclosure, a use of standard design rules for design of independent layers of a microfluidic cartridge is illustrated. As long as these design rules are followed, layers in the cartridge can be added, removed, or replaced in a plug and play fashion. We also illustrate a versatile testing setup that can test individual layers or any combination of layers as long as the design rules are followed. The same testing setup can also be used for efficient mass chemical modification of many cartridge layers at once.

SUMMARY OF THE INVENTION

According to one aspect of the present invention, a stacked testing assembly comprises a microfluidic cartridge for analyzing a fluid sample and a testing setup. Said microfluidic cartridge includes a number of layers stacked in a height direction with many different kinds of combinations. Said testing setup is capable of assembling and testing all kinds of said layers combinations with no change to the setup.

According to a second aspect of the present invention, a microfluidic cartridge comprises a set of layers stacked in a height direction. Each of said layer defines a standard number of via ports passing therethrough in the height direction for connecting non-adjacent layers to one another and being closed on the current layer only if the layer needs to receive fluid sample from said non-adjacent layer, and a standard number of alignment holes passing therethrough in the height direction and locating at corners thereof to align the layers during assembly of said layers.

According to a third aspect of the present invention, a microfluidic cartridge for analyzing a fluid sample including at least two different types of particles comprises a counter layer defining first flow channels formed thereon to count all types of particles for a first testing, a capture layer stacked with said counter layer to capture at least one type of said particles, an electrode layer stacked with said counter layer and defining a set of electrodes disposed thereon; said counter layer further defines second flow channels formed thereon to count remaining types of particles for a second testing after said capture layer capturing said particles of interest; said electrodes are disposed in the first and second flow channels to detect the particles flowing in the first and second flow channels respectively.

Other objects, advantages and novel features of the invention will become more apparent from the following detailed description when taken in conjunction with the accompanying drawings.

DETAILED DESCRIPTION OF THE PREFERRED EMBODIMENT

Figure 1:
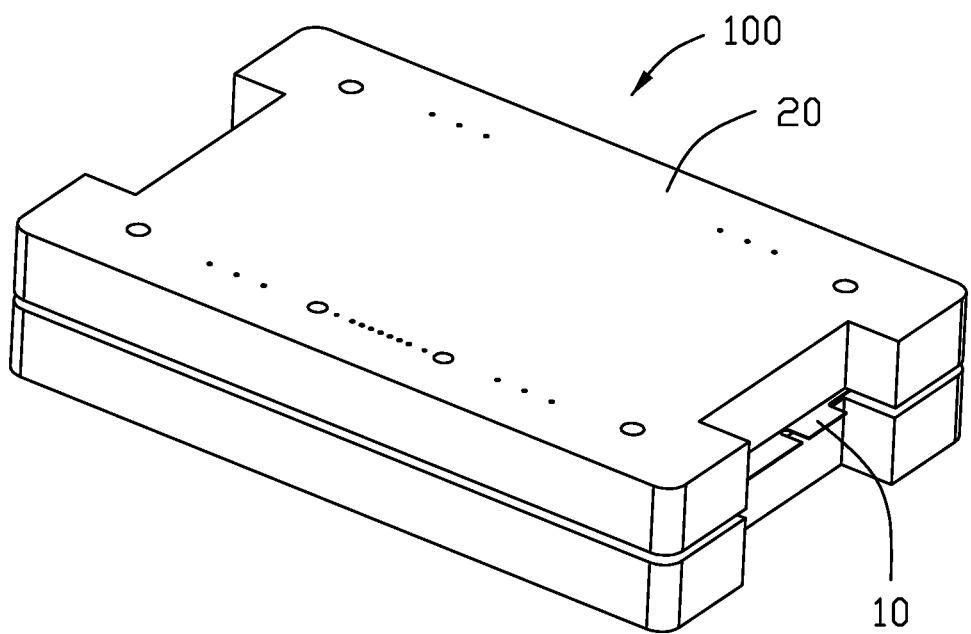
FIG. 1 is a perspective view of a stacked testing assembly in accordance with a first embodiment of the present invention.
Figure 2:
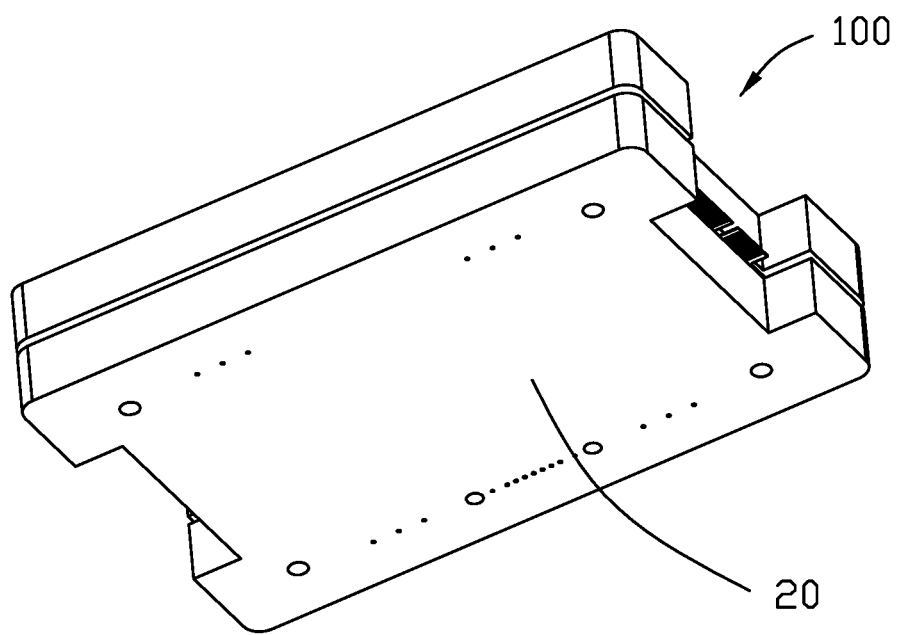
FIG. 2 is another perspective view of the stacked testing assembly shown in FIG. 1.
Figure 3:
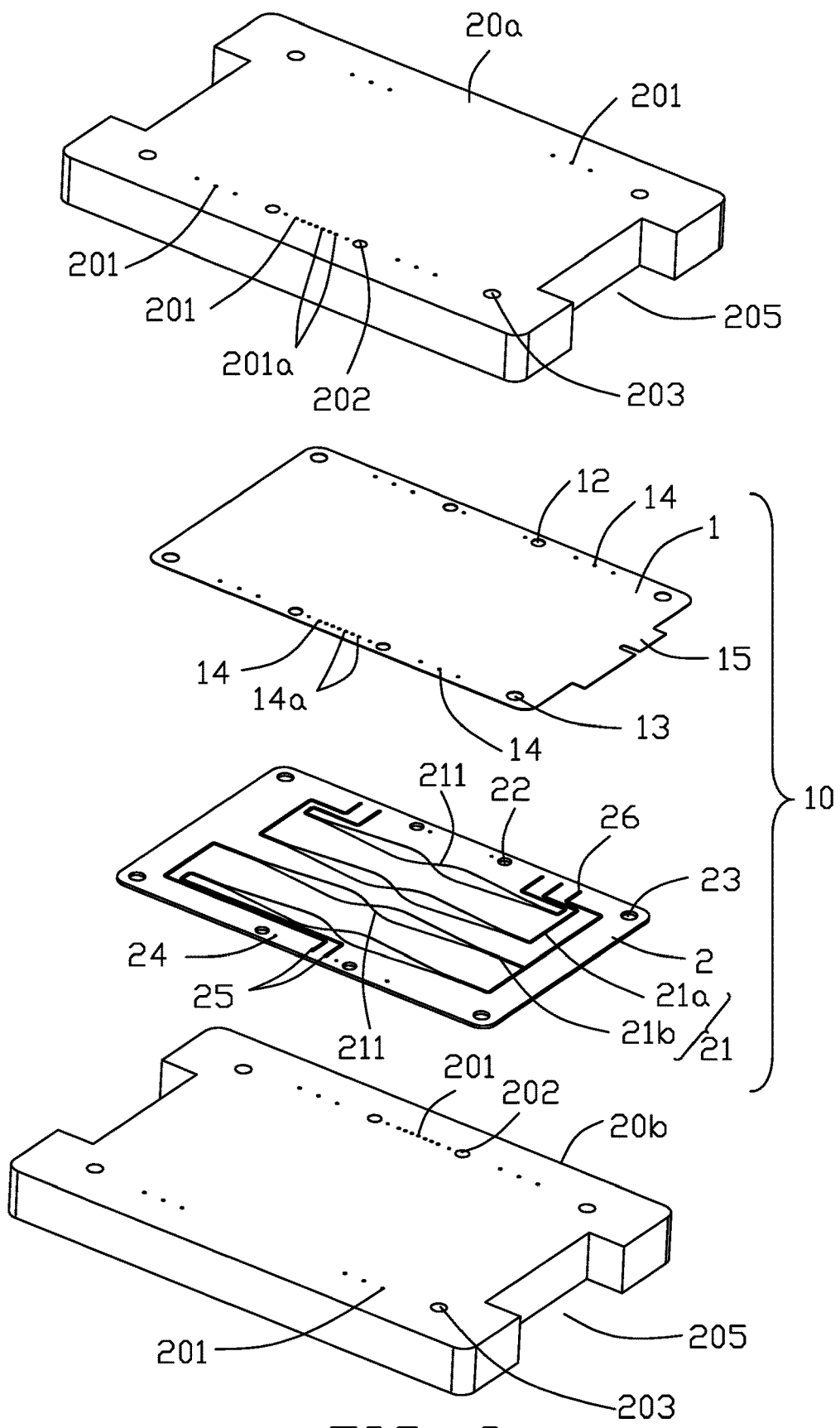
FIG. 3 is an exploded view of the stacked testing assembly shown in FIG. 1.
Figure 4:
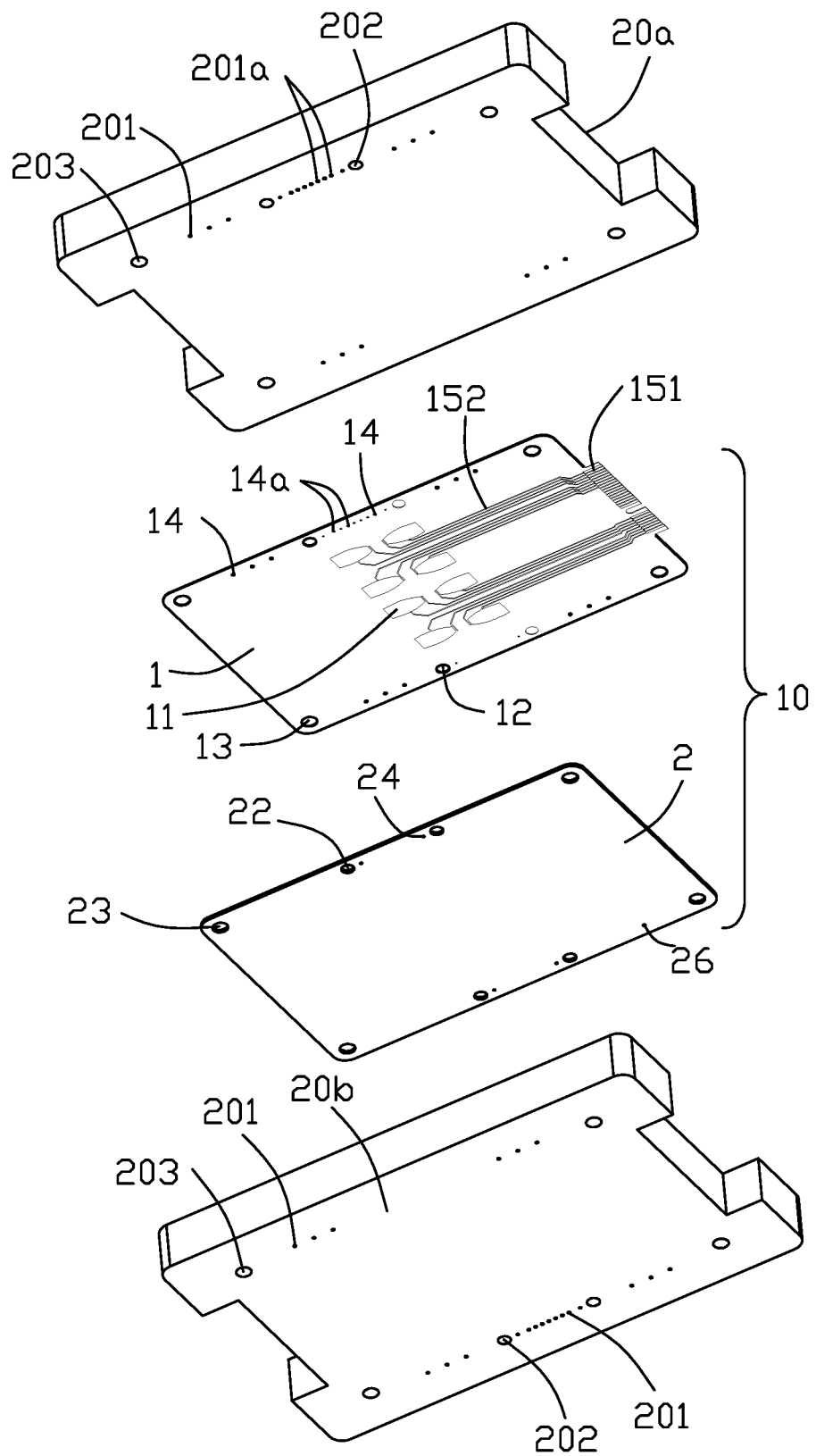
FIG. 4 is another exploded view of the stacked testing assembly show in FIG. 1.

Referring to FIGS. 1-4, a stacked testing assembly 100 according to a first embodiment of the present invention includes a microfluidic cartridge 10 and a testing setup 20 for assembling and testing layers of said microfluidic cartridge 10. Said microfluidic cartridge 10 according to the present invention is provided for fluid sample analyses such as counting cells, measuring the concentration of cell surface molecules, or measuring the concentration of biomarkers in plasma or serum.

Referring to FIGS. 3-8. the microfluidic cartridge 10 in this first embodiment can be used to profile a fluid sample only. The microfluidic cartridge 10 includes a first and second layers 1, 2 stacked in a height direction. The first and second layers 1, 2 may be made of various materials used in microfluidics, including but not limited to polydimethylsiloxane (PDMS), Cyclic olefin co-polymer, acrylic, or any other material commonly used for microfluidics. These materials could be milled, embossed, injection molded, or any other techniques used to form microfluidic channels. The first layer 1 is an electrode layer and defines a set of electrodes 11 arranged on a lower side thereof. The second layer 2 is a counter layer containing Coulter counters (defined by electrodes that induce an electric field across an aperture for counting particles) and defines four flow channels 21 formed on an upper side thereof. Each flow channel 21 forms a detecting region 211 for detecting particles 500 of the fluid sample. The detecting region 211 has detection aperture with a size larger than that of each particle 500 so as to prevent clogging and make sure the particles 500 pass through the detecting region 211 singly. The detecting region 211 defines an entry 2111 at an upstream thereof for a single particle 500 entering into at a time, and an exit 2112 at a downstream thereof for a single particle 500 exiting out at a time.

The electrodes 11 include four pairs of electrodes 11 arranged in four rows in the width direction. These electrodes must make contact with the fluid overlaying the channels to induce an electric field across the detection region. Each pair of electrodes 11 are disposed in one the detecting regions 211 and between the entry 2111 and the exit 2112, and the electrodes 11 align in a line along the flow direction of the fluid sample. Therefore, the particles 500 of the fluid sample pass over the two or four electrodes 11 successively in the detecting region, and the electrodes 11 could simply and conveniently detect whether or not any particles 500 pass through the detecting region 211, the size of the particles, and the time required for the passage of the particles, etc on basis of the resistance, capacitance, or opacity variations between the two electrodes 11. Furthermore, each electrode 11 strides across the detecting region 211 in the width direction of the detecting region 211 so as to detect the particles 500 reliably.

Figure 6:
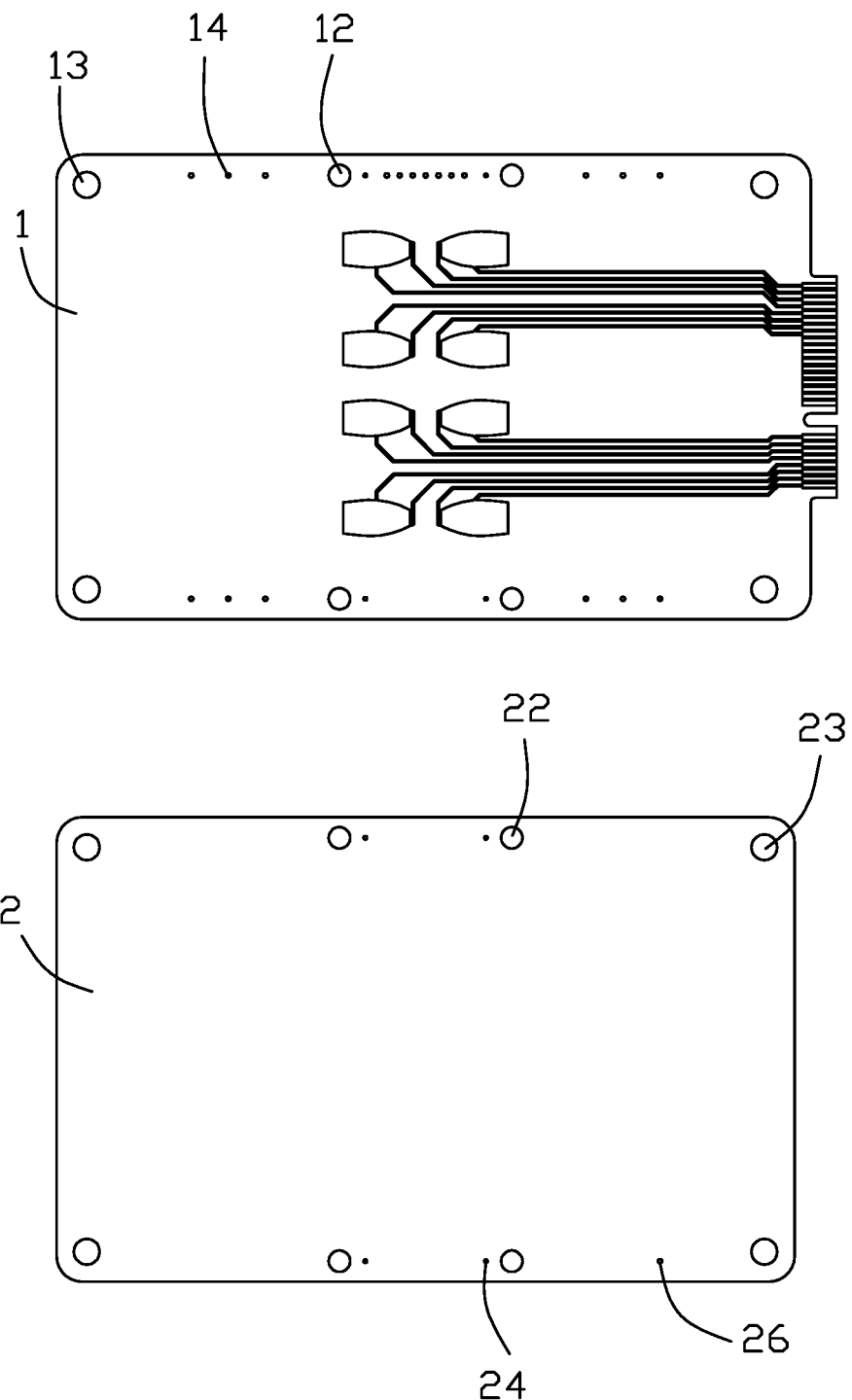
FIG. 6 is a bottom elevation view of the exploded microfluidic cartridge shown in FIG. 4.
Figure 7:
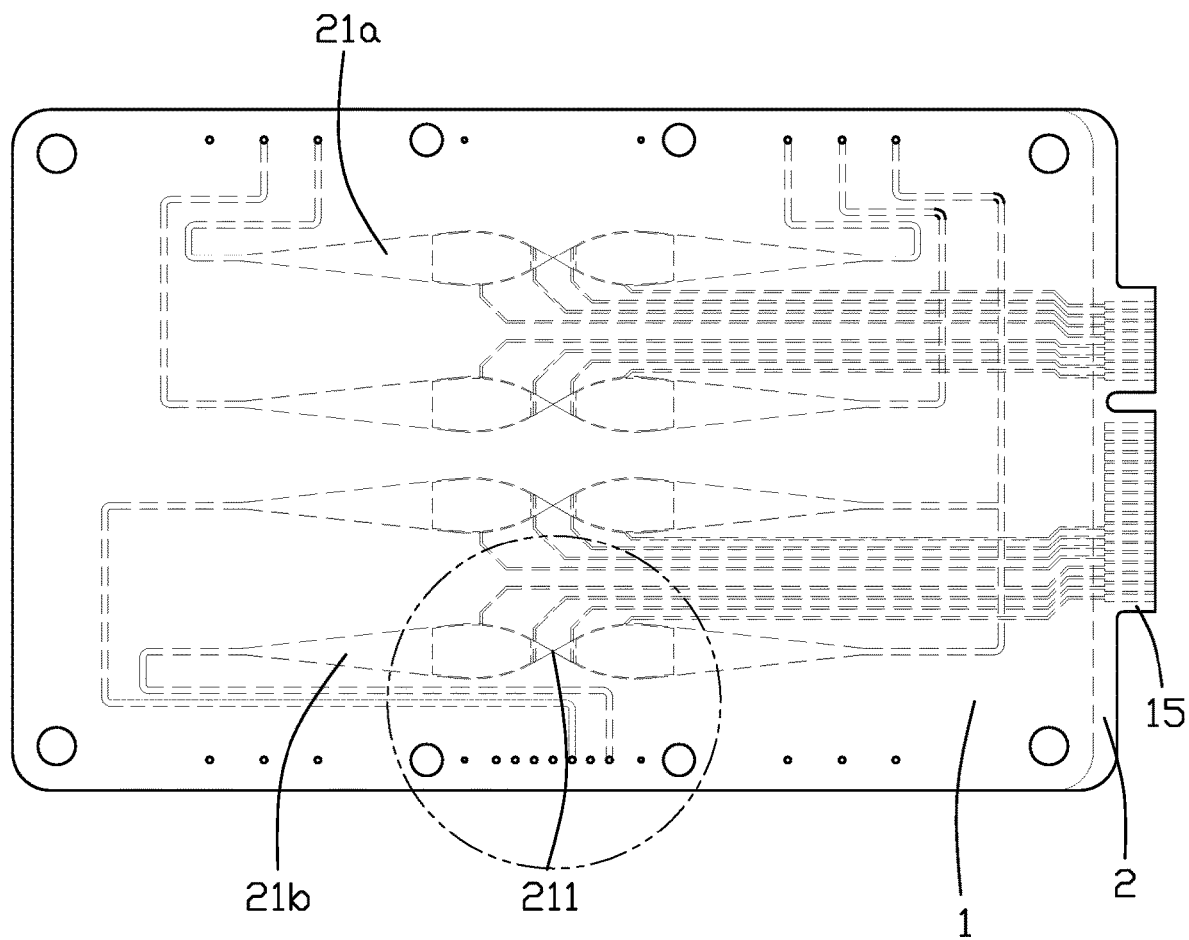
FIG. 7 is a planar schematic diagram showing the construction of the microfluidic cartridge.
Figure 8:
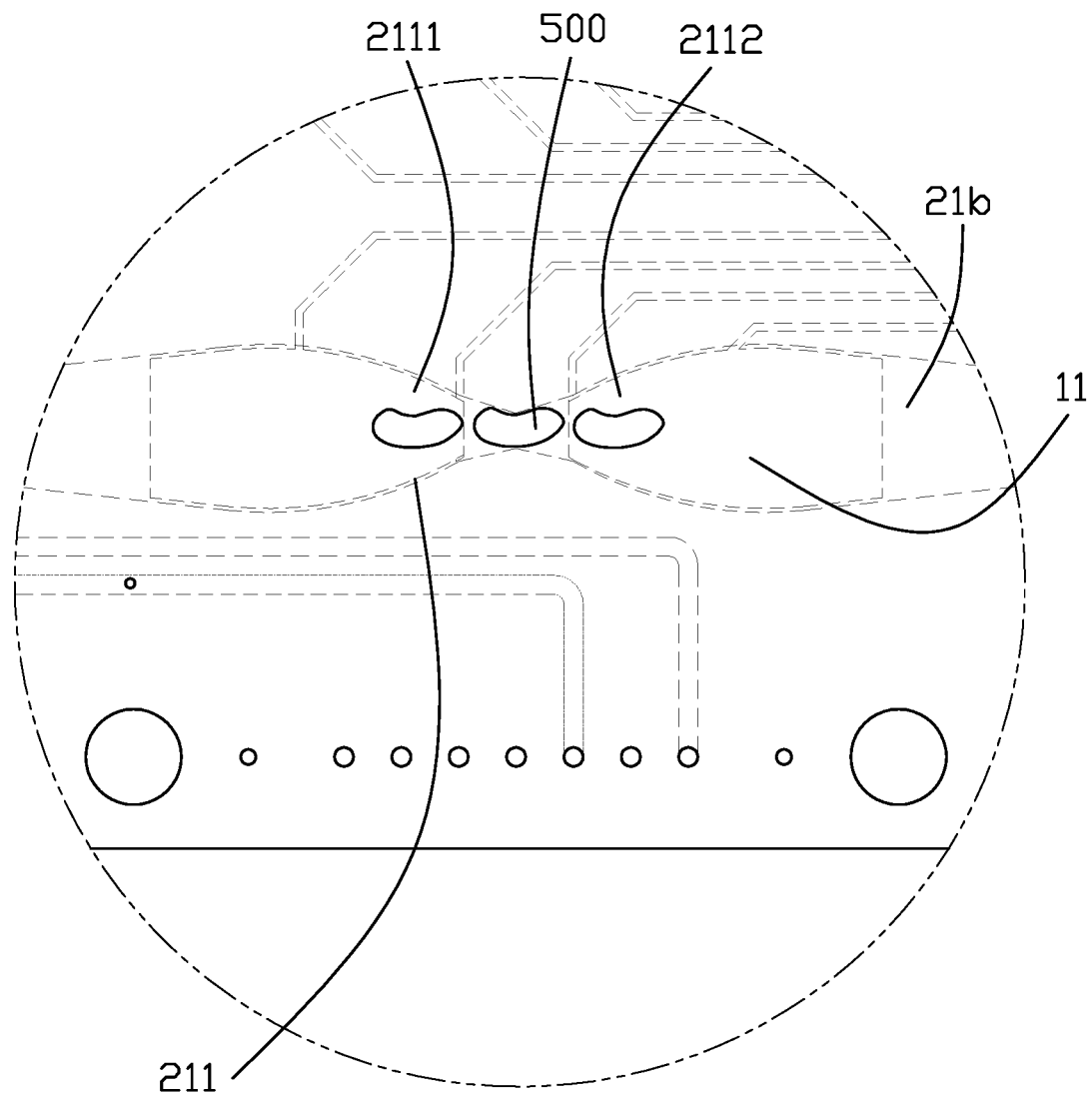
FIG. 8 is an enlarged diagram showing fluid sample passing through the detecting region shown in FIG. 7.
Figure 9:
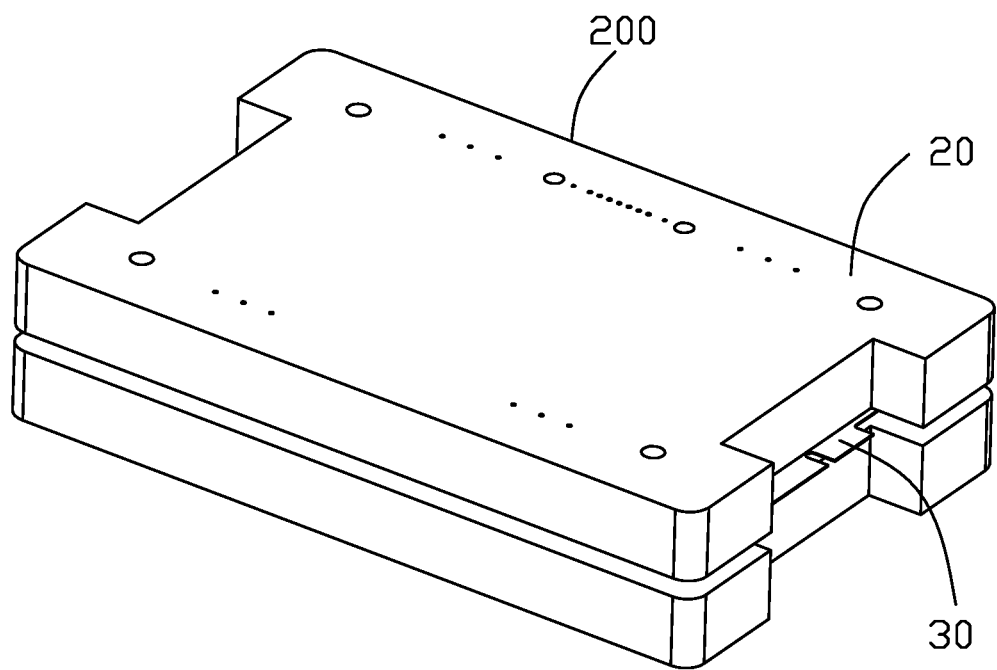
FIG. 9 is a perspective view of a stacked testing assembly in accordance with a second embodiment of the present invention.
Figure 10:
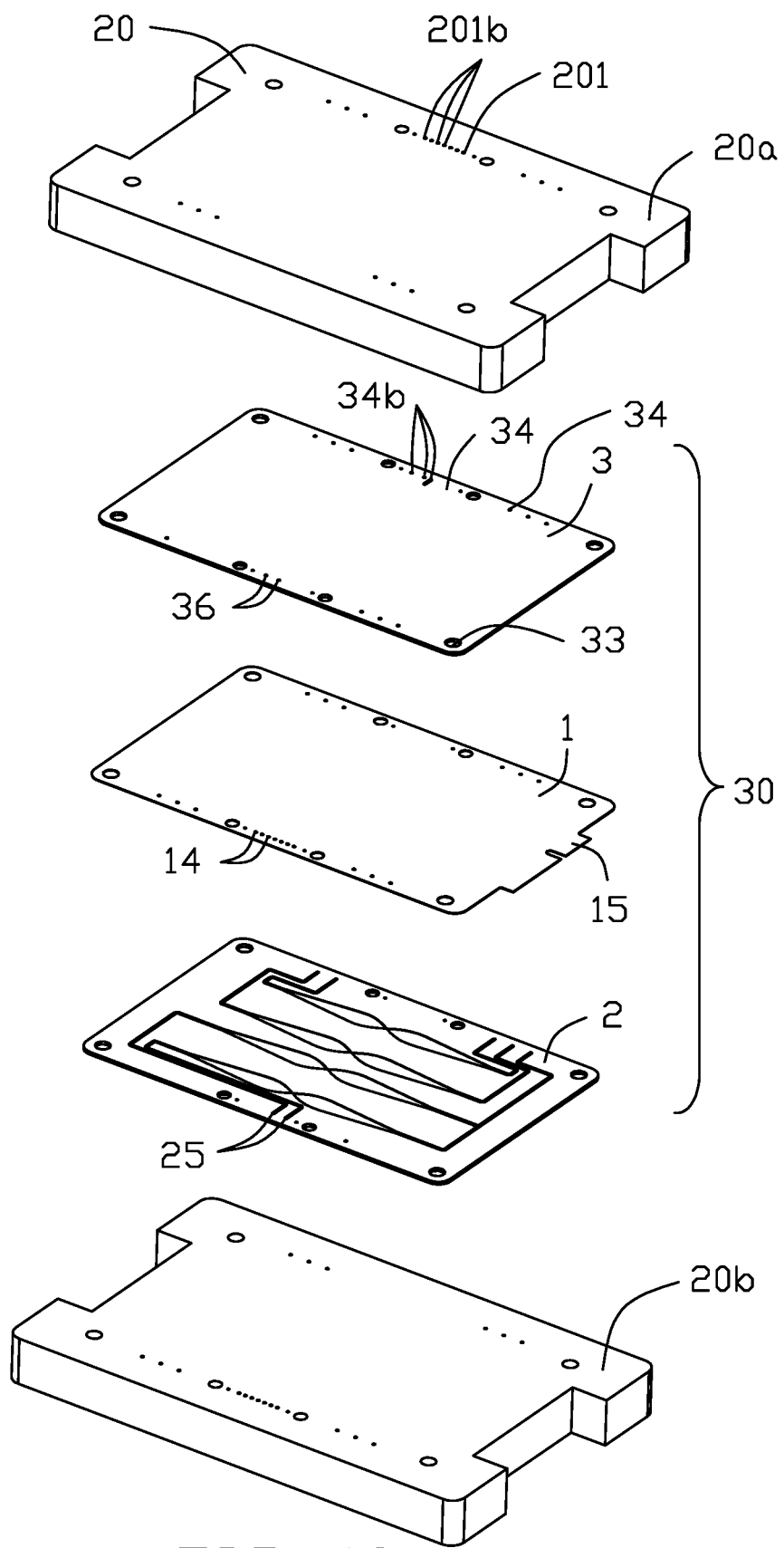
FIG. 10 is an exploded view of the stacked testing assembly show in FIG. 9.
Figure 11:
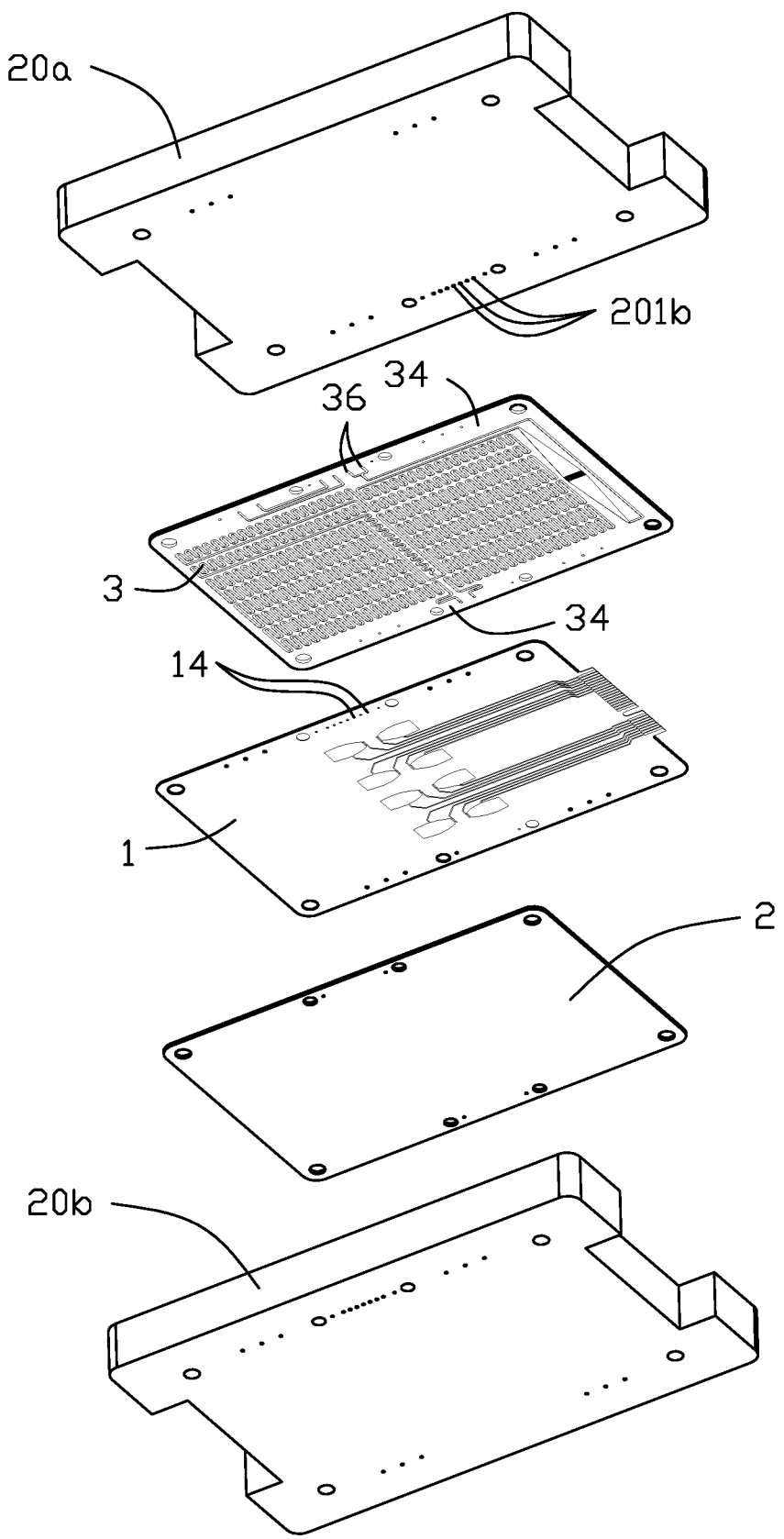
FIG. 11 is another exploded view of the stacked testing assembly show in FIG. 9.
Figure 12:
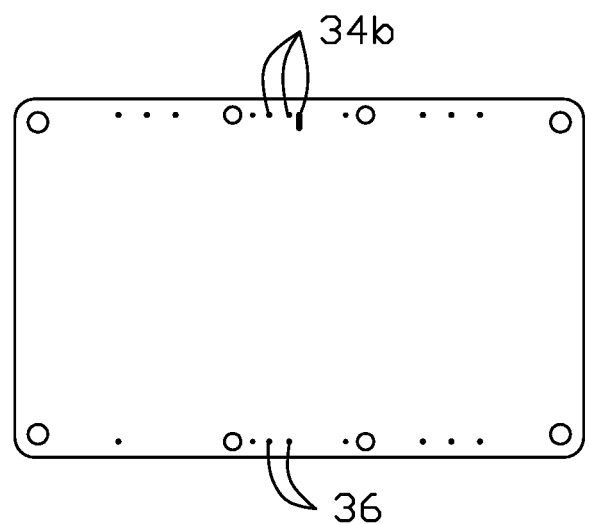
FIG. 12 is a top elevation view of the exploded microfluidic cartridge show in FIG. 10.
Figure 12:
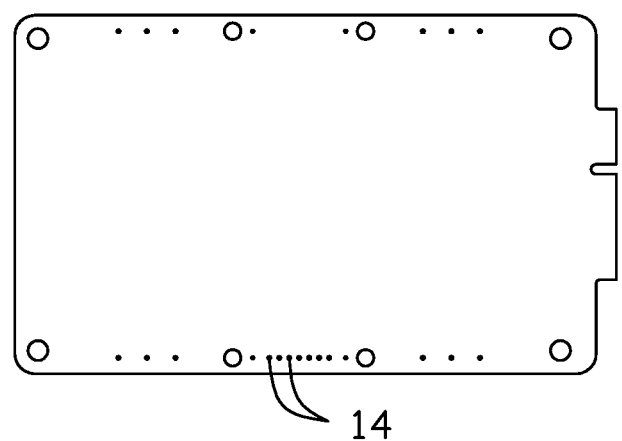
Figure 12:
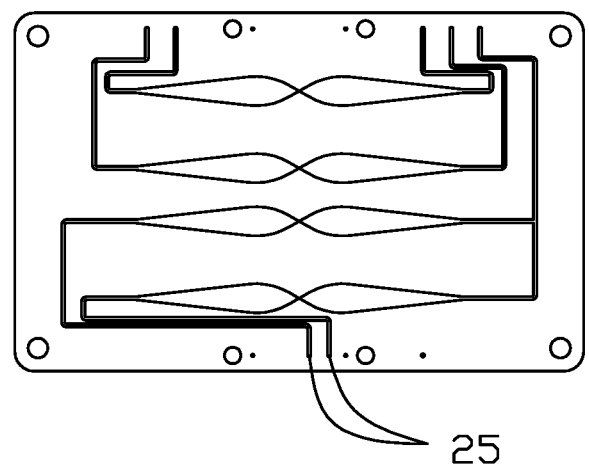
Figure 13:
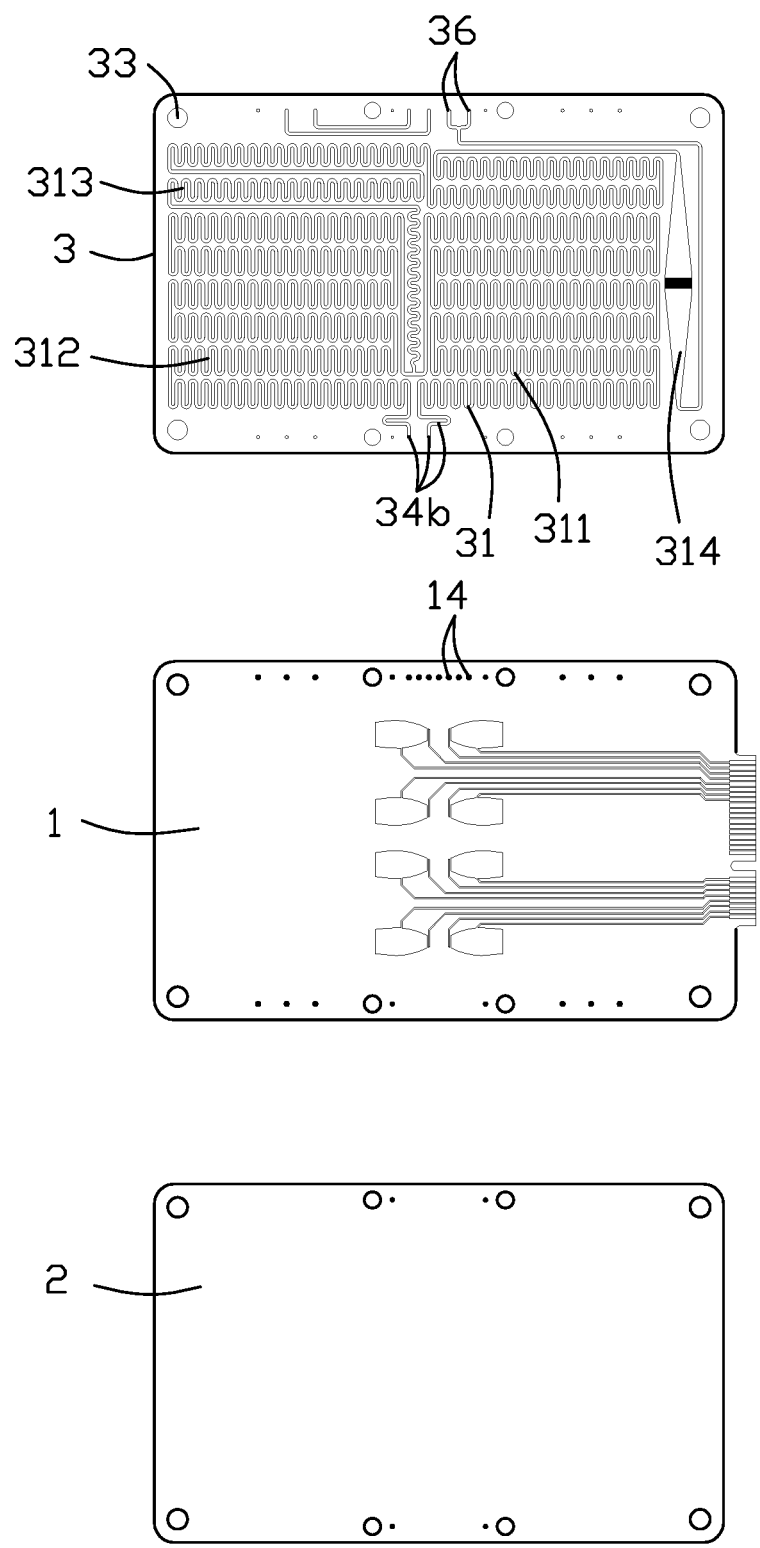
FIG. 13 is a bottom elevation view of the exploded microfluidic cartridge shown in FIG. 11.
Figure 14:
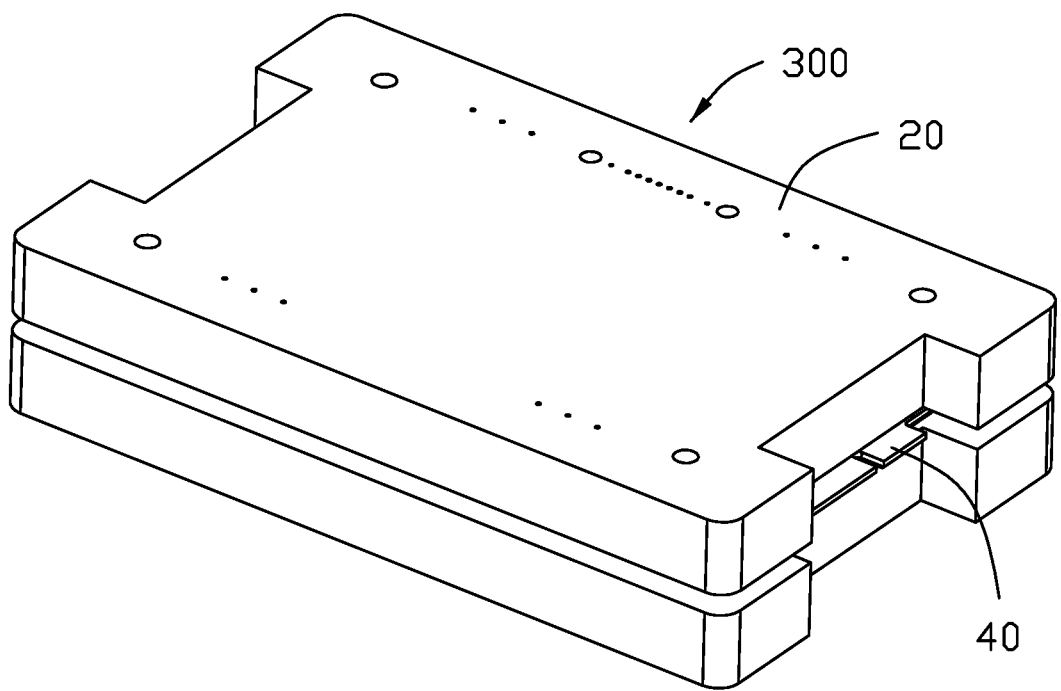
FIG. 14 is a perspective view of a stacked testing assembly in accordance with a third embodiment of the present invention.
Figure 15:
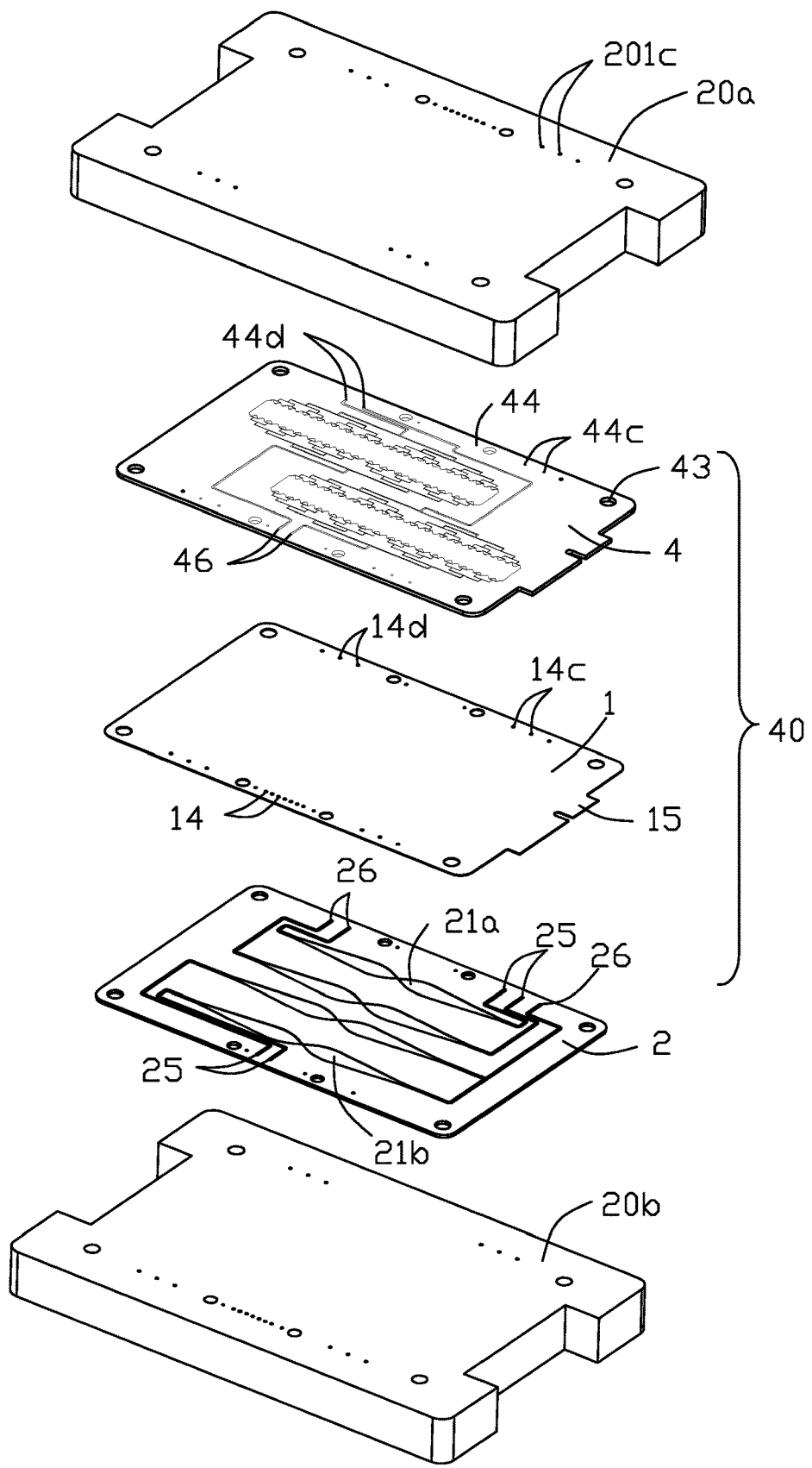
FIG. 15 is an exploded view of the stacked testing assembly show in FIG. 14.
Figure 16:
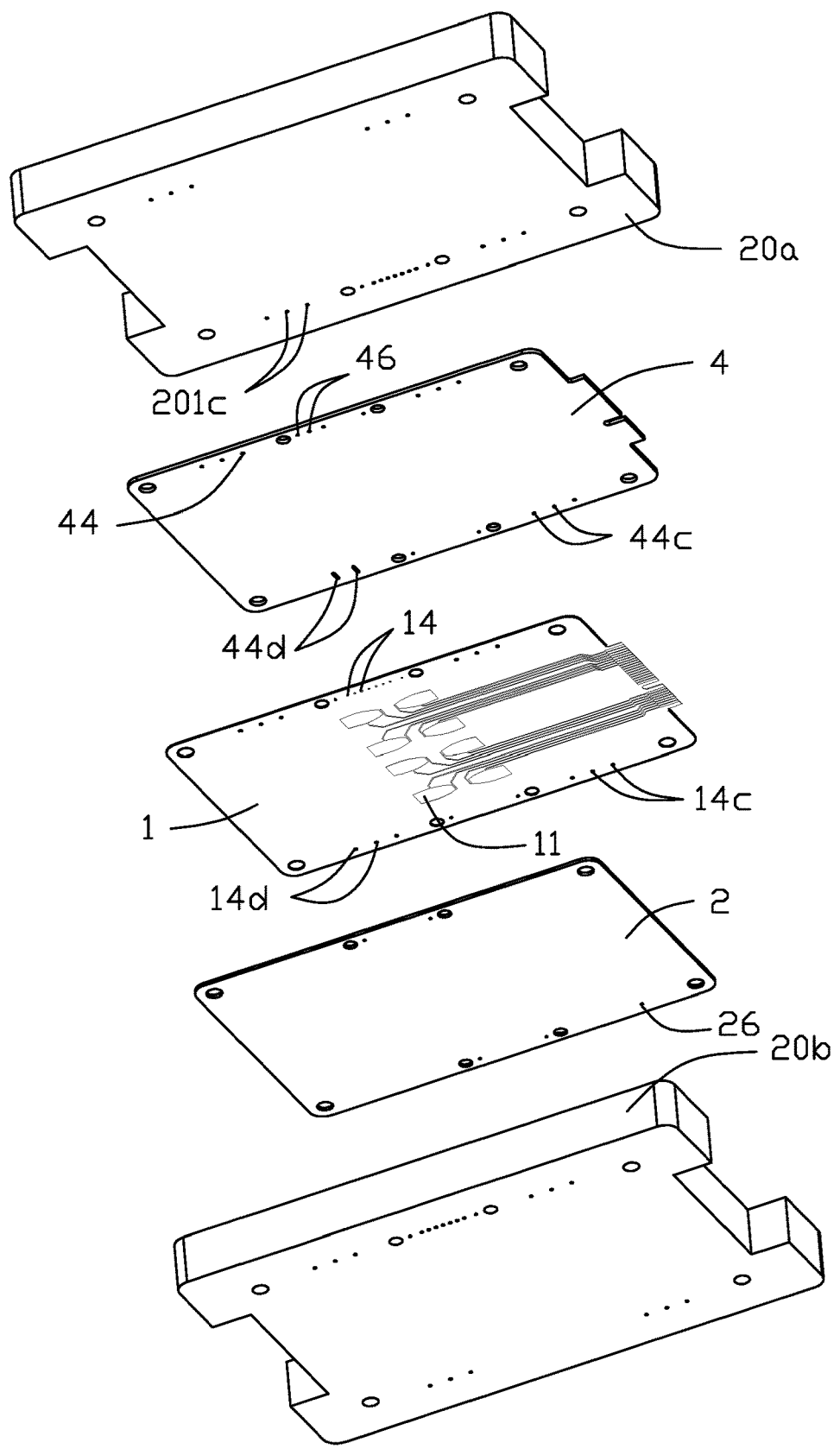
FIG. 16 is another exploded view of the stacked testing assembly show in FIG. 14.
Figure 17:
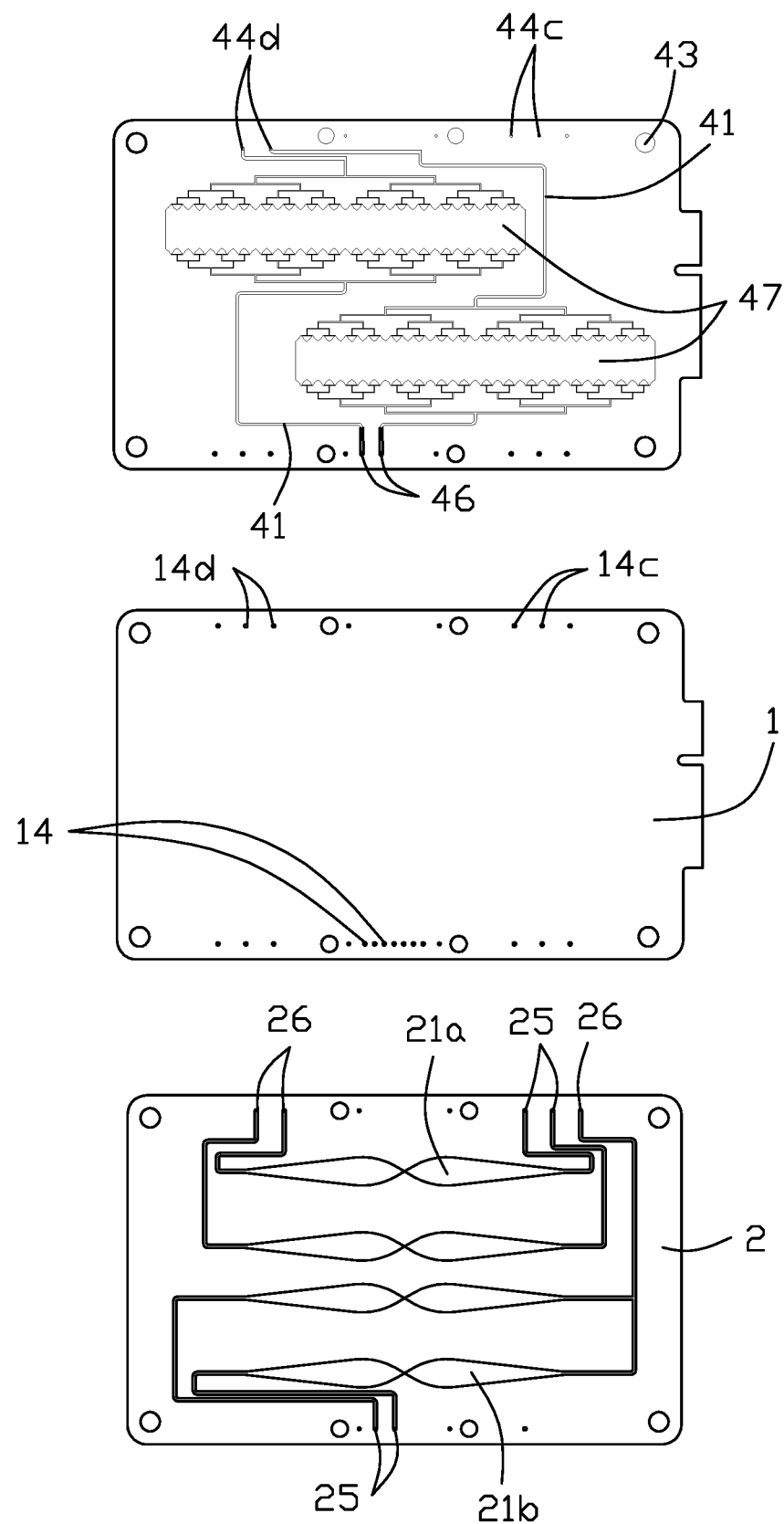
FIG. 17 is a top elevation view of the exploded microfluidic cartridge show in FIG. 15.
Figure 18:
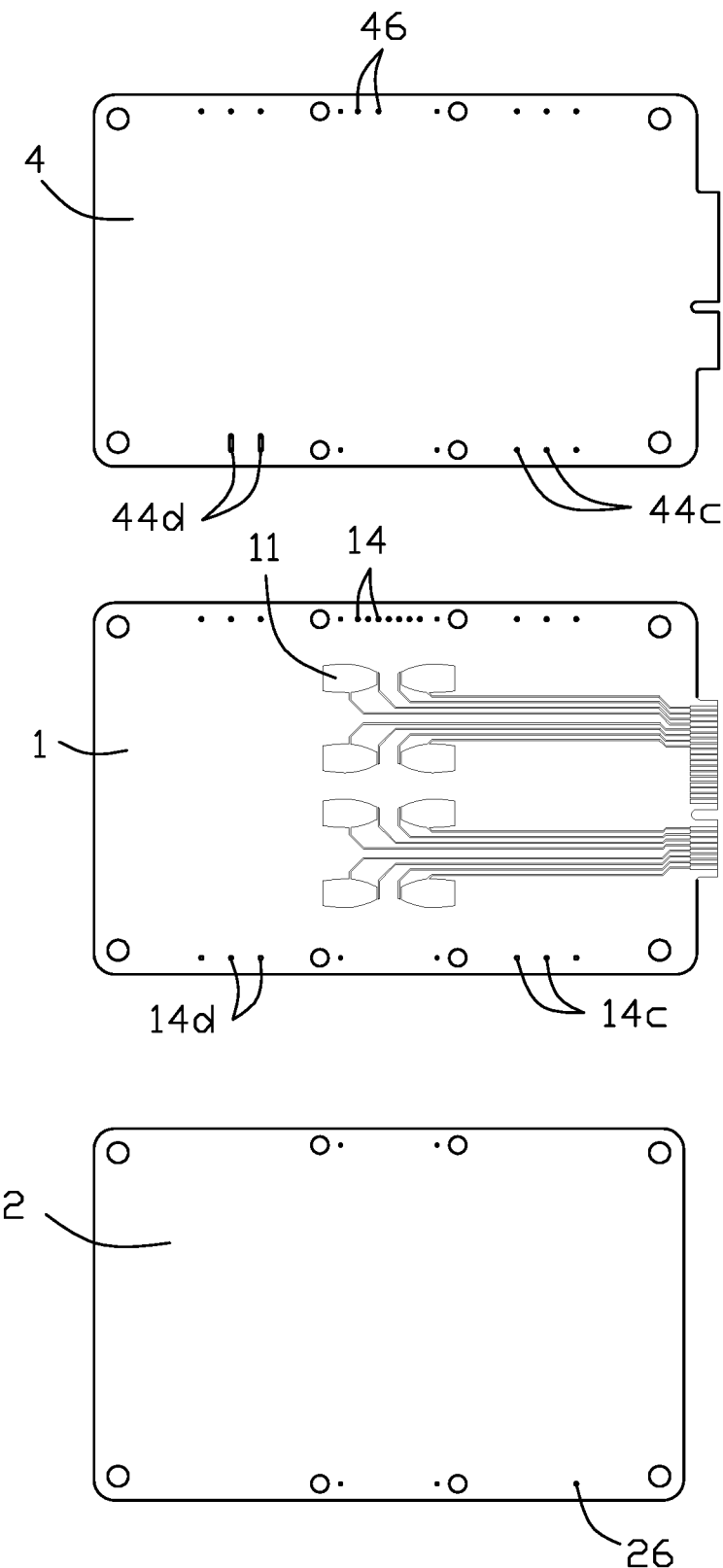
FIG. 18 is a bottom elevation view of the exploded microfluidic cartridge shown in FIG. 16.
Figure 19:
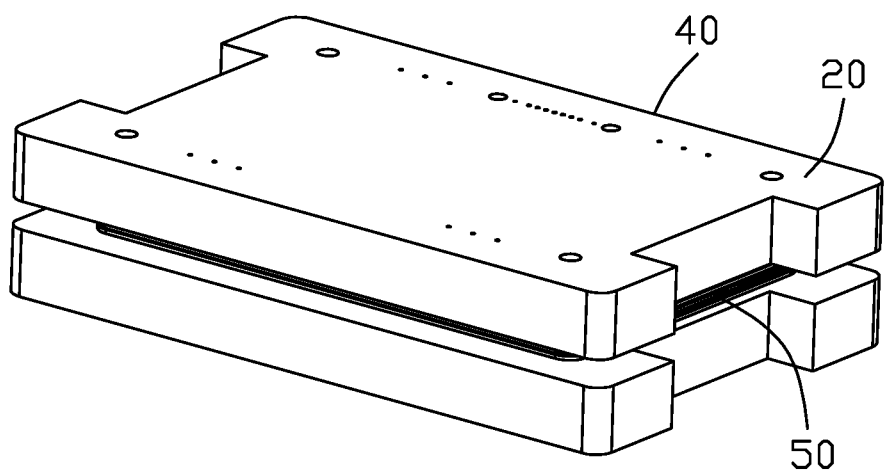
FIG. 19 is a perspective view of a stacked testing assembly in accordance with a fourth embodiment of the present invention.
Figure 20:
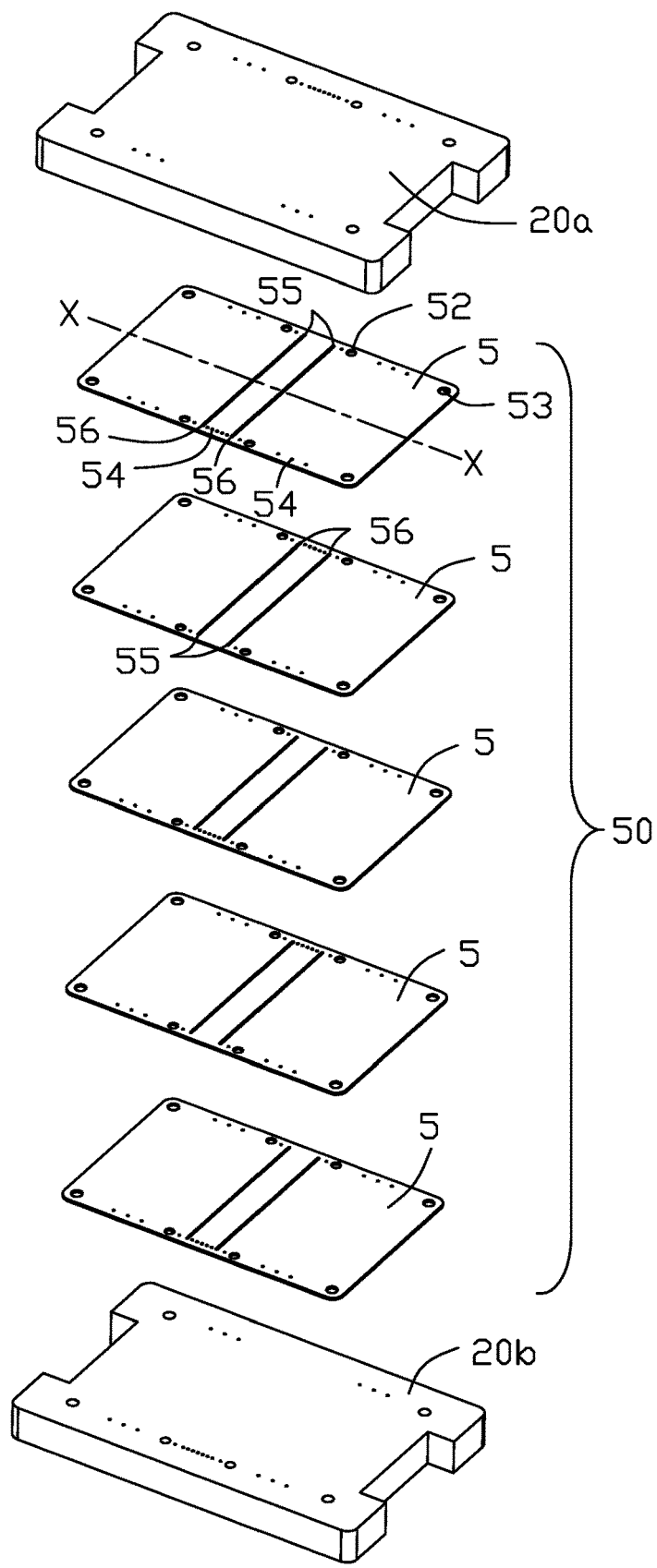
FIG. 20 is an exploded view of the stacked testing assembly show in FIG. 19.
Figure 21:
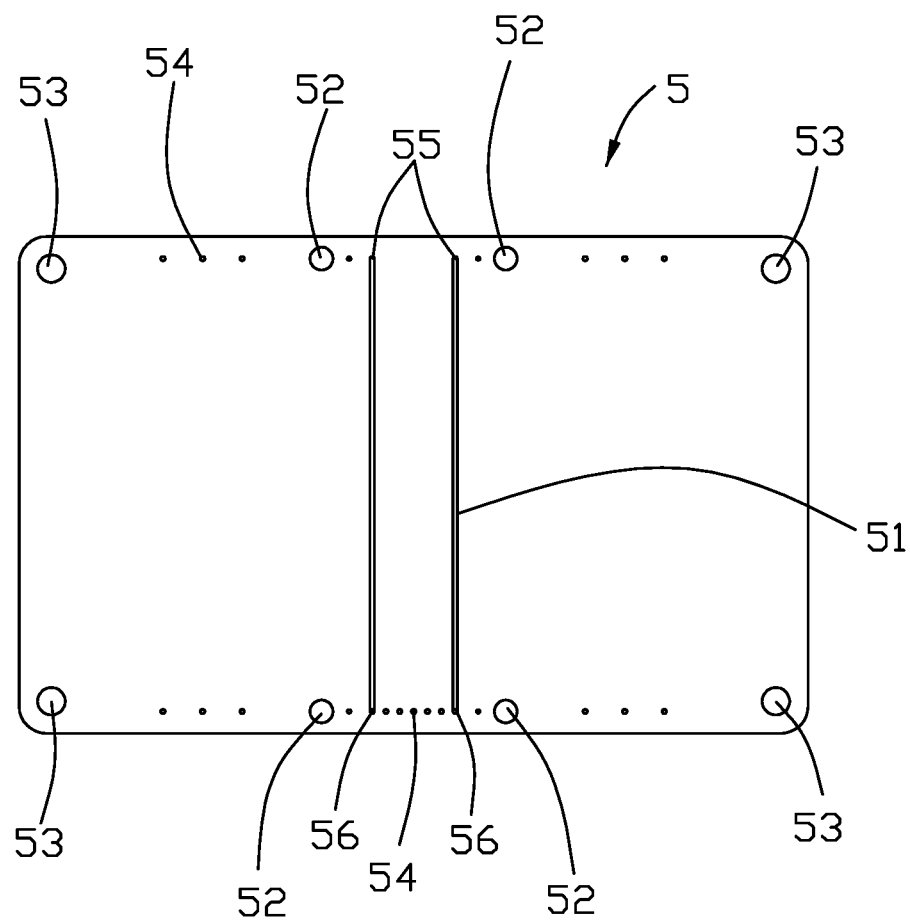
FIG. 21 is a top elevation view of a layer of a microfluidic cartridge show in FIG. 20.
Figure 22:
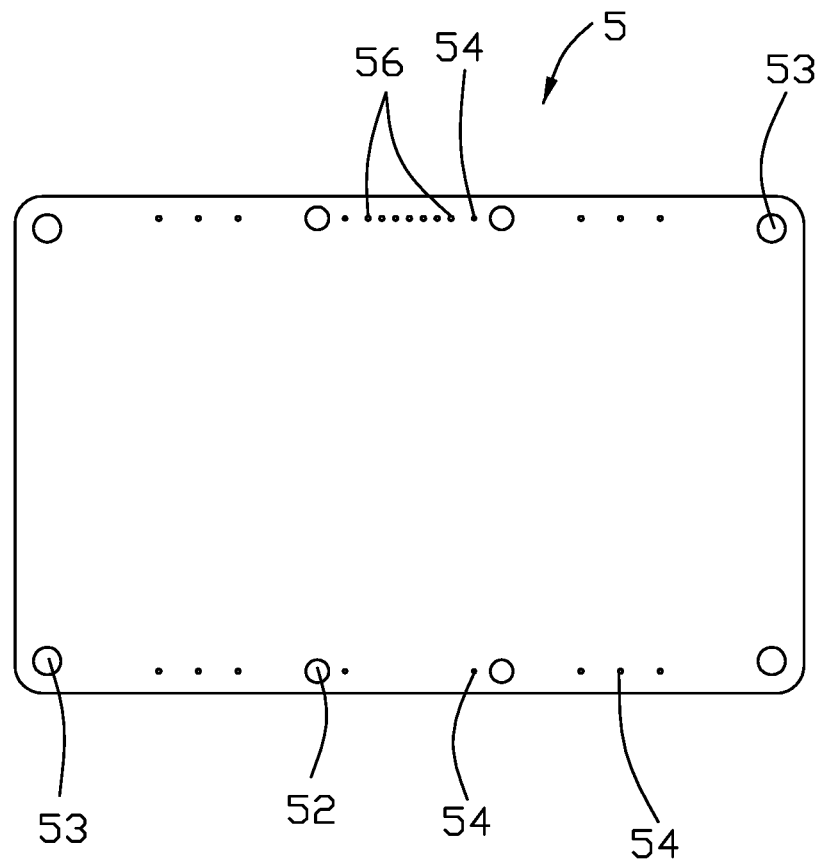
FIG. 22 is a bottom elevation view of the layer of the microfluidic cartridge shown in FIG. 21.
Figure 23:
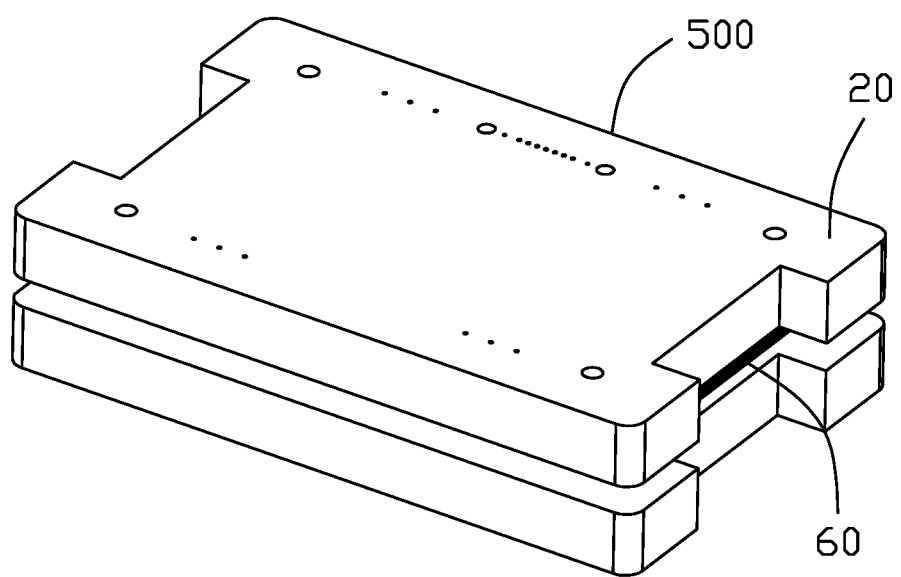
FIG. 23 is a perspective view of a stacked testing assembly in accordance with a fifth embodiment of the present invention.
Figure 24:
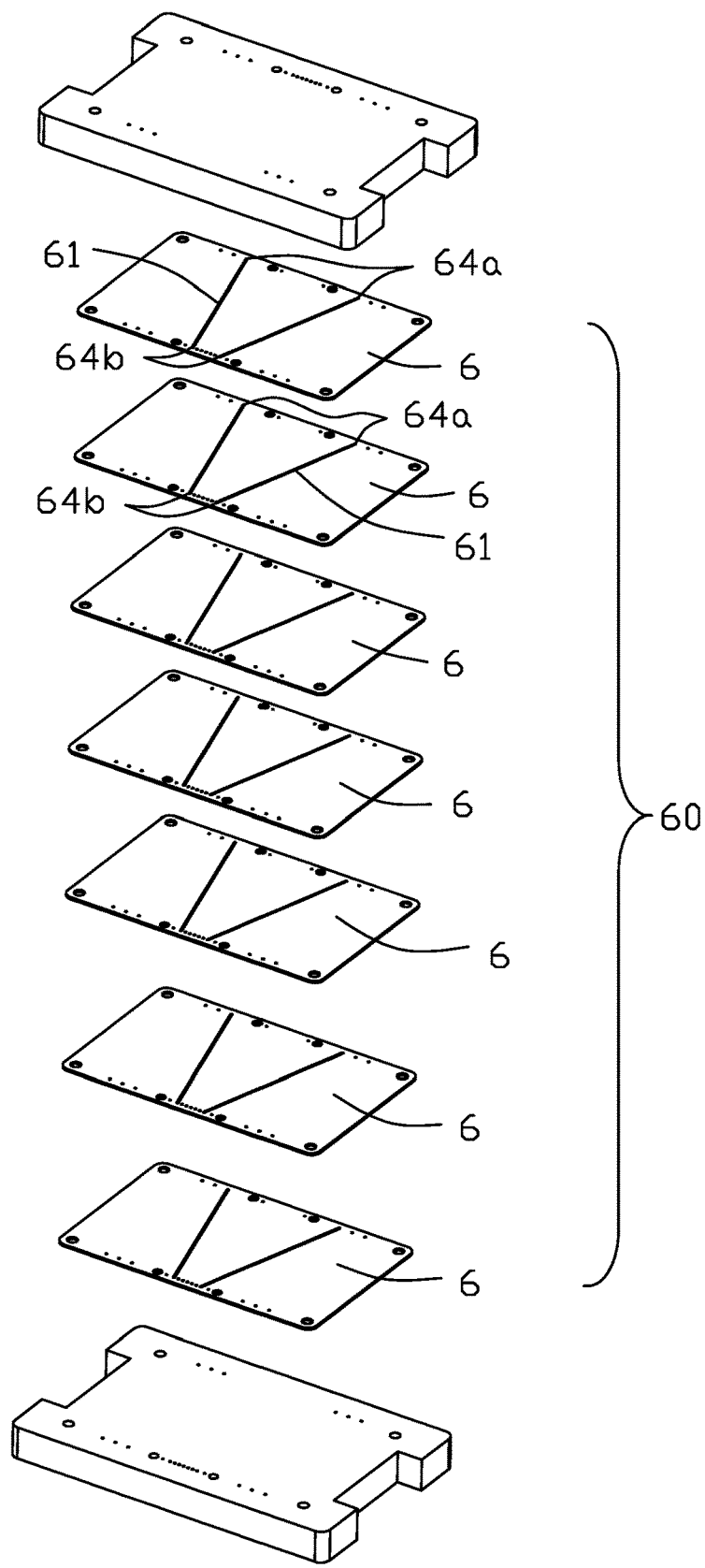
FIG. 24 is an exploded view of the stacked testing assembly show in FIG. 23.
Figure 25:
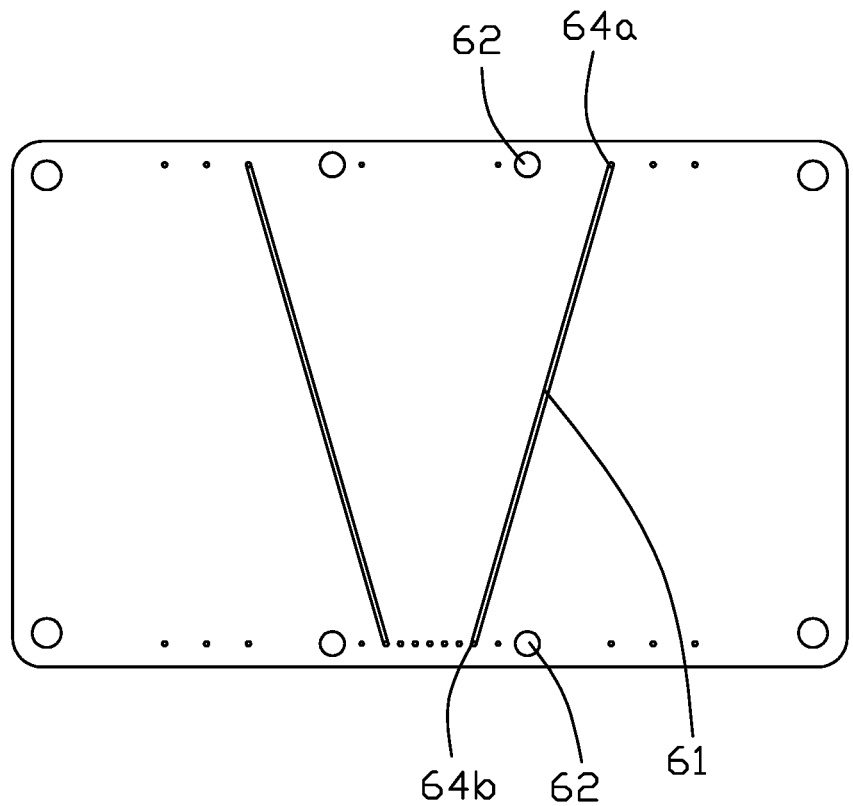
FIG. 25 is a top elevation view of a layer of a microfluidic cartridge show in FIG. 24.
Figure 26:
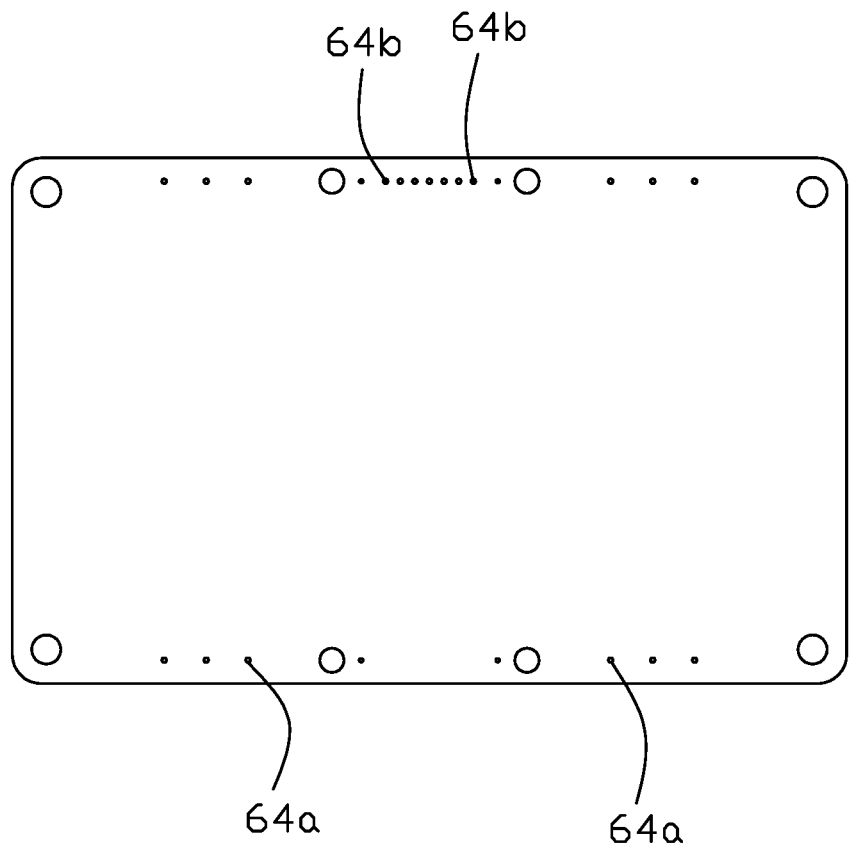
FIG. 26 is a bottom elevation view of the layer of the microfluidic cartridge shown in FIG. 25.
Figure 27:
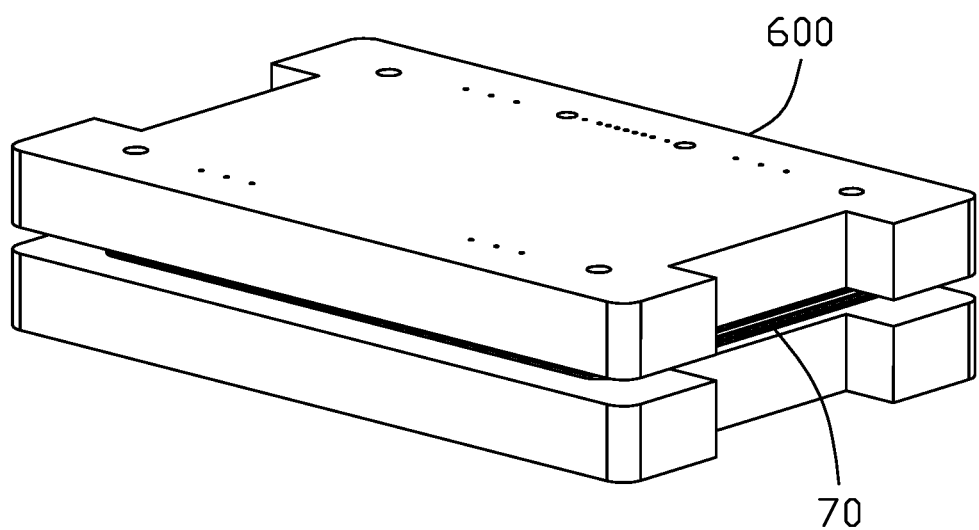
FIG. 27 is a perspective view of a stacked testing assembly in accordance with a sixth embodiment of the present invention.
Figure 28:
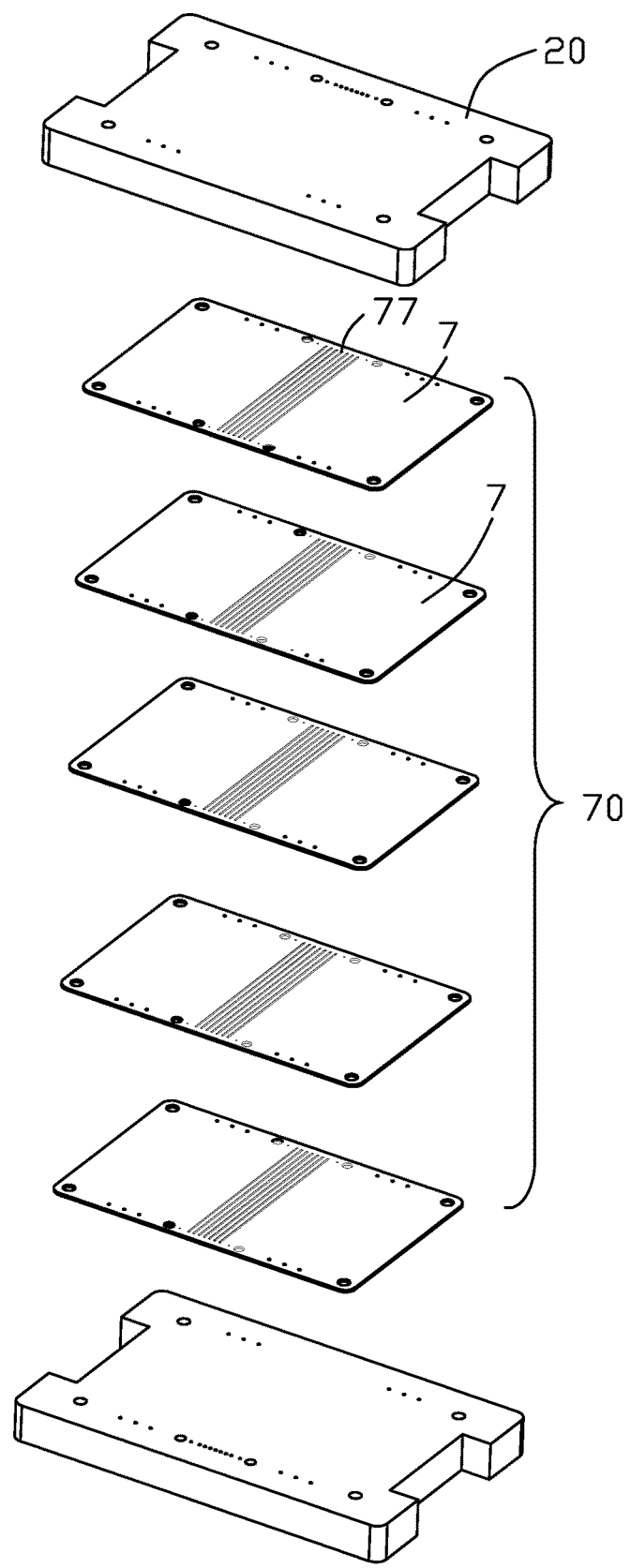
FIG. 28 is an exploded view of the stacked testing assembly show in FIG. 27.
Figure 29:
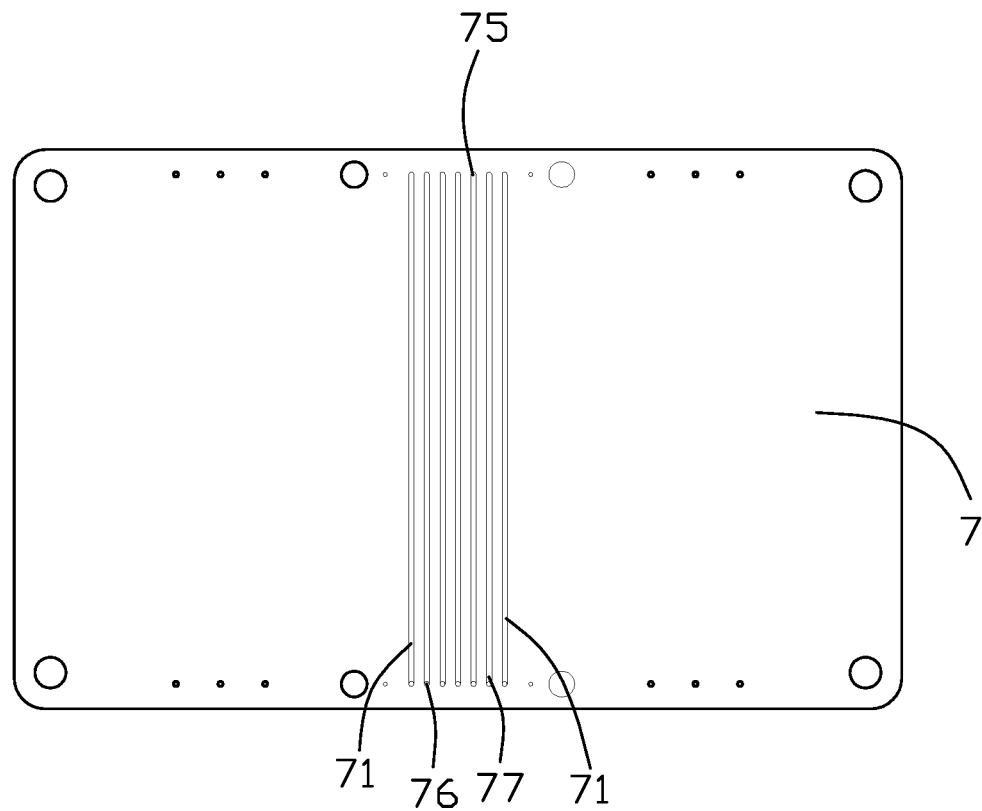
FIG. 29 is a top elevation view of a layer of a microfluidic cartridge show in FIG. 28.
Figure 30:
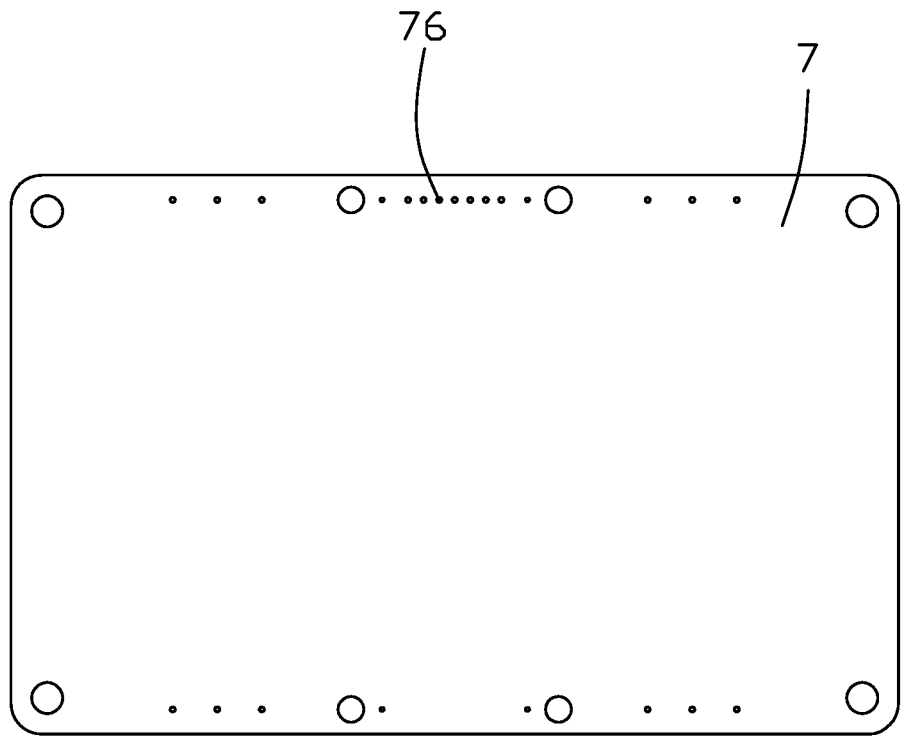
FIG. 30 is a bottom elevation view of the layer of the microfluidic cartridge shown in FIG. 29.

Referring to FIG. 6, the first layer 1 has a tongue portion 15 protruding from one end thereof in a longitudinal direction perpendicular to the height direction. A set of pads 151 are formed on a lower side of the tongue portion 15 and connect to the electrodes 11 respectively via electrical traces 152.

Referring to FIGS. 3-6, both the first and second layers 1,2 include a set of alignment holes 13,23 passing therethrough in the height direction to align the first and second layers 1, 2 using guide pins during assembly of the first and second layers 1,2. The alignment holes 13, 23 of each of the first and second layers 1, 2 are four and locate at corners of the respective first and second layers 1, 2 symmetrically. Both of the first and second layers 1, 2 include two pairs of fixture holes 12, 22 locating at two sides thereof in a width direction. The first layer 1 defines a set of via ports 14 with standard size, pitch, and location, these via ports 14 are through holes passing through the first layer 1. The second layer 2 defines a set of via ports 24, a set of input ports 25 recessed from an upper side thereof and do not penetrate a lower side thereof, and a set of output ports 26. The output ports 26 are through holes passing through the second layer 2, the input ports 25 and output ports 26 are connected by the flow channels 21 respectively. The first layer 1 and second layer 2 could be sealed to one another only by using positive pressure, negative pressure, or positive plus negative pressure to achieve the desired flow through the stack, or by using reversible double sided pressure sensitive adhesives between, or by any other reversible or irreversible bonding techniques.

Figure 5:
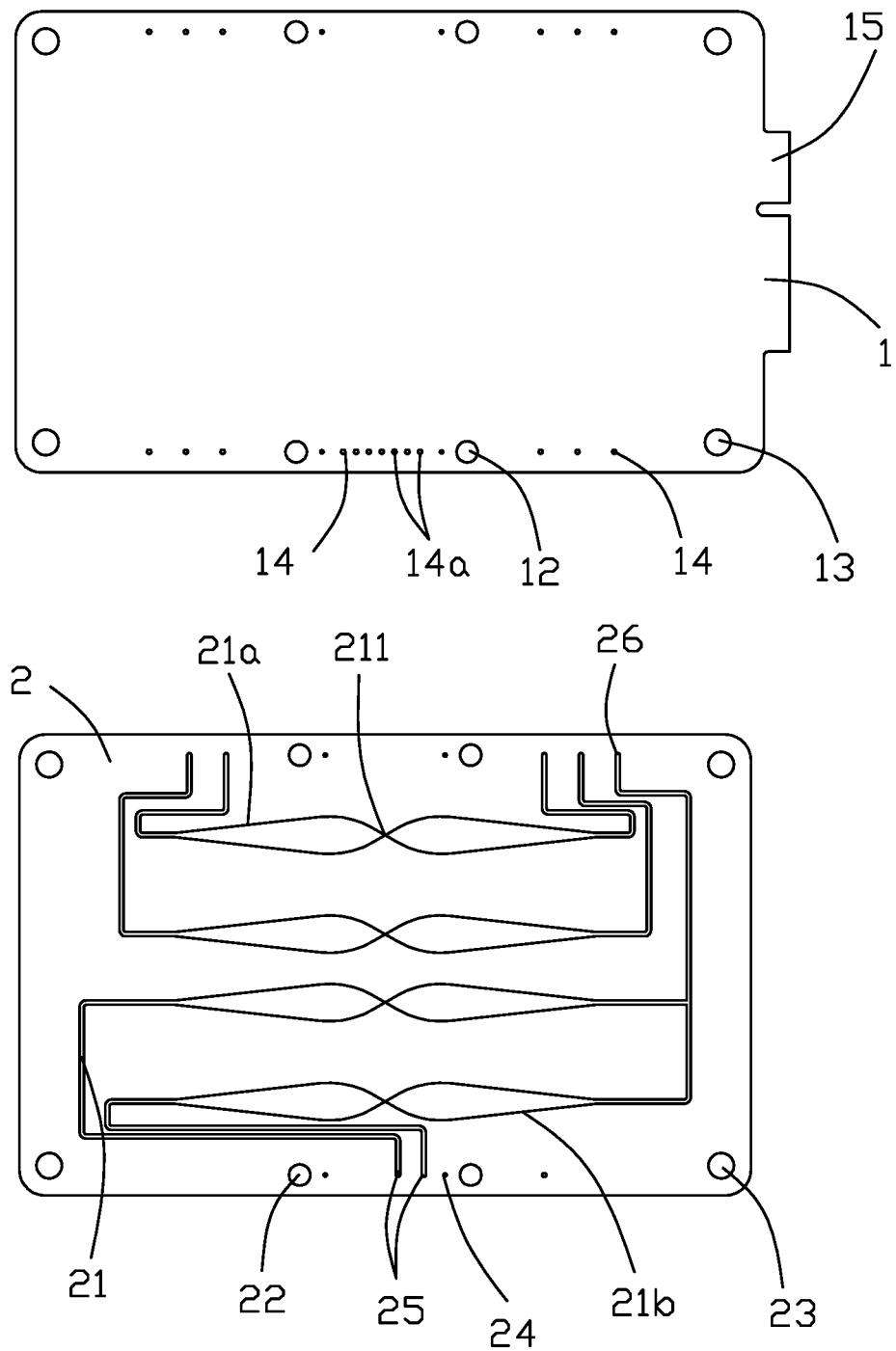
FIG. 5 is a top elevation view of the exploded microfluidic cartridge show in FIG. 3.

Referring to FIG. 5, the four flow channels 21 are arranged as a pair of first flow channels 21a and a pair of second flow channels 21b. The first flow channels 21a are separate from each other all the time at both upstream and downstream sides of the detecting region 211 in said first flow channels 21a. The second flow channels 21b are separate from each other at upstream sides and are merged into one channel at downstream sides of the detecting region 211 in said second flow channels 21b. At least two different measurements from a fluid sample could be detected from the same microfluidic cartridge 10 in the first embodiment.

Referring to FIGS. 1-4, the testing setup 20 includes a pair of identical upper and lower clamping members 20a, 20b clamping said first and second layers 1, 2 therebetween so as to assembled said layers of said microfluidic cartridge 10 together. Each clamping member 20a, 20b defines four alignment holes 203 passing therethrough in the height direction and locating at corners of said clamping members 20a, 20b so as to align to the respective alignment holes 13, 23 of the first and second layers 1, 2. Each clamping member 20a, 20b defines a set of through holes 201 passing therethrough in the height direction and locating at right and left sides and a pairs of fixture holes 202 locating at one side in the width direction.

Eight of said through holes 201 locate between said fixture holes 202 of the clamping members 20a, 20b and are used for connecting with a microfluidic connector (not shown), the fixture holes 202 align with the fixture holes 12, 22 of the first and second layers 1, 2 and are used for mounting said microfluidic connector thereon. The upper and lower clamping members 20a, 20b in the first embodiment locates at a mirror image symmetry, in detail, the fixture holes 202 of the upper clamping member 20a locate at the right side, while the fixture holes 202 of the lower clamping member 20b locate at the left side. The through holes 201 of the upper clamping member 20a align to and connect with the respective via ports 14 of the first layer 1. Some through holes 201 of the lower clamping member 20b align to and connect with the output ports 26 of the second layer 1. Each clamping member 20a, 20b defines a pair of cutouts 205 at two ends in the longitudinal direction, the tongue portion 15 of the first layer 1 exposes on the respective cutout 205.

Referring to FIGS. 1-8, when the testing setup 20 assemble said first and second layers 1, 2 of the microfluidic cartridge 10 together for testing, the tongue portion 15 connect with a socket connector of a interrogation platform (not shown) so as to test the stacked testing assembly 100. Two of said through holes 201 indicated as 201a are introduced for testing via the microfluidic connector; the fluid samples pass through the first layer 1 via the respective via ports indicated as 14a and enter the input ports 25 of the pair of second flow channel 21b; the fluid samples flow in the second flow channels 21b, the particles 500 of the fluid samples pass over the respective electrodes 11 successively in the detecting regions 211 so as to finish the testing, then the fluid samples enters the respective output port 26 of the second flow 21b and finally flow into the through holes 201 of the lower clamping member 20b for being discharged.

Referring to FIGS. 9-13, a stacked testing assembly 200 according to a second embodiment of the present invention. The testing setup 20 can also assemble and test layers of a microfluidic cartridge 30. The microfluidic cartridge 30 further includes a third layer 3 stacked with the first and second layers 1, 2.

The third layer 3 is mixing layer and could be used for lysing of the fluid sample before the particles entering the via ports 14 of the first layer 1. The third layer 3 stacks on an upper side of the first layer 1 and defines a set of via ports 34 with standard size, pitch, and location, these via ports 34 are through holes passing through the third layer 3, the via ports 34 are closed on the third layer 3 by the first layer 1 pressing against so as to receive fluid sample from said testing setup. The third layer 3 also defines a set of aliment holes 33 and a set of output ports 36, the output ports 36 are through holes passing through the third layer 3 and align to the via ports 14 of the first layer 1. The third layer 3 defines a wandering groove 31 on a lower side thereof, the wandering groove 31 includes a lysis mixing section 311, a quench flow section 312, a quench mixing section 313, and a filter section 314. Said lysis mixing section 311 and quench flow section 312 separate from each other at the beginnings and meet together at the ends; said quench mixing section 313 extends from said meet point to the filter section 314.

Referring to FIGS. 9-13, when the testing setup 20 assemble said first, second and third layers 1, 2, 3 of the microfluidic cartridge 30 together for testing, the tongue portion 15 connect with a socket connector of a interrogation platform (not shown) so as to test the stacked testing assembly 200. Three of said through holes 201 indicated as 201b are introduced with fluid sample, lysis solution, and quench solution respectively. The lysis solution and said fluid sample enter the via ports indicated as 34b and flow into the lysis mixing section 311 so as to mix with each other sufficiently, therefore the rate of the fluid sample flowing in the groove 31 will be boosted effectively, the quench solution enter the via ports 34 and flow into the quench section 312, and then meet with the lysed fluid sample at the quench mixing section 313 so as to quench lysis of said fluid sample, the fluid sample passes over the filter section 314 so as to remove any particles which may block the via ports, input ports and output ports, Coulter apertures, or narrow channels. Then the fluid sample enters two output ports 36 of the third layer 3, passes through the via ports 14 of the first layer 1 and enter the input ports 25 of the second layer 2, the remaining processes are same as that of the first embodiment, therefore, the detail descriptions of the remaining processes are omitted here.

Referring to FIGS. 14-18, a stacked testing assembly 300 according to a third embodiment of the present invention. The testing setup 20 can also assemble and test layers of a microfluidic cartridge 40. The microfluidic cartridge 40 further includes a fourth layer 4 stacked with the first and second layers 1, 2.

The fourth layer 4 is a capture layer and used for capturing particles of interest from the fluid sample. The fourth layer 4 stacks on an upper side of the first layer 1 and defines a set of via ports 44 with standard size, pitch, and location, these via ports 44 are through holes passing through the fourth layer 4. The fourth layer 4 defines a set of alignment holes 43 passing therethrough in the height direction to align that of the first and second layers 1, 2, and a set of output ports 46 which are through holes passing through the fourth layer 4 and align to the via ports 14 of the first layer 1. The fourth layer 4 defines a pair of capture chambers 47 on an upper side thereof, the capture chambers 47 connect with input ports 45 and the output ports 46 respectively via flow channels 41.

Referring to FIGS. 14-18, when the testing setup 20 assemble said first, second and fourth layers 1, 2, 4 of the microfluidic cartridge 40 together for testing, the tongue portion 15 connect with a socket connector of a interrogation platform (not shown) so as to test the stacked testing assembly 300. Two of said through holes 201 indicated as 201c are introduced with two kinds of fluid samples with many different types of particles. The fluid samples pass through via ports indicated as 44c of the fourth layer 4 and the via ports indicated as 14c of the first layer 1, and enters the input ports 25 of the first flow channels 21a; the fluid sample flows in the first flow channels 21a, the total types of particles pass over the respective electrodes 11 successively in the detecting regions so as to detect total types of the particles and finish the first testing; then the fluid sample enters the respective output port 26 of the first flow channels 21a and upwardly passes through the via ports indicated as 14d of the first layer 1 and via ports indicated as 44d of the fourth layer 4 to flow into the flow channels 41, the capture chambers 47 capture the selective particles of the fluid sample of interest onto surfaces of the chamber using binding moieties such as analyte capture or binding agents and controlled shear; the remaining particles of the fluid sample enter the output ports 46 of the fourth layer 4, pass through the via ports 14 of the first layer 1 and enter the input ports 25 of the second flow channels 21b; the remaining particles flow in the second flow channels 21b, pass over the respective electrodes 11 successively in the detecting regions so as to detect the remaining particles and finish the second testing, then the remaining fluid sample enters the respective output port 26 and finally flow into the through holes 201 of the lower clamping member 20*b* for being discharged. Therefore, the number of the selective particles of the fluid sample of interest captured by the capture layer 4 could be calculated by subtracting the number of the remaining particles in the second testing from the number of the total types of the particles in the first testing.

Referring to FIGS. 19-22, a stacked testing assembly 400 according to a fourth embodiment of the present invention. The testing setup 20 can also assemble and test layers of a microfluidic cartridge 50. The microfluidic cartridge 50 includes a set of standardized layers 5 stacked in the height direction.

Referring to FIGS. 19-22, each layer 5 defines a standard number of via ports 54 with standard size, pitch, and location, the via ports 54 are through holes passing through the layer 5 in the height direction and are used to connect non-adjacent layers to one another, the via ports 54 are closed on the current layer only if the current layer needs to receive fluid sample from a non-adjacent layer. Each layer 5 defines a standard number of alignment holes 53 passing therethrough in the height direction to align the layers 5 using guide pins during assembly of the layers 5, the alignment holes 53 in this embodiment are four and locate at corners of the layers 5. Each layer 5 defines two pairs of fixture holes 52 passing therethrough in the height direction and locating at two sides thereof in a width direction perpendicular to the height direction, the fixture holes 52 passes through the layers 5 in the height direction and are smaller than the alignment holes 53 in this embodiment. Each layer 5 defines a standard number of input ports 55 with standard size, pitch, and location; the input ports 55 recess from one side thereof in the height direction while do not penetrate the other opposite side, the input ports 55 are used to communicate with a neighbouring layer. Each layer 5 defines a standard number of output ports 56 with standard size, pitch, and location; the output ports 56 are through holes passing through the current layer 5 to align to and connect the input ports 55 of a neighbouring layer, the input ports 55 and output ports 56 in each layer 5 correspond to each other and locate at opposite ends of flow channels 51 respectively.

All of the fixture holes 52, alignment holes 53, via ports 54, input ports 55 and output ports 56 are disposed along edges of the layers 5 and are arranged in two rows in the longitudinal direction. In this embodiment, two input ports 55 and two output ports 56 are formed on each layer, and all of the input ports 55 and output ports 56 locate between the respective pairs of fixture holes 52 in the longitudinal direction; the input ports 55 and output ports 56 locate in two rows separately, and the input ports 55 align to the corresponding output ports 56 in the width direction; two flow channels 51 are formed on a same side of each layer and extend straightly and parallelly. In this embodiment every two adjacent layers 5 are arranged in a mirror image symmetry manner along a central line X-X in the longitudinal direction, the fluid sample therefore will flow through every single layer serially (one layer at a time) and that each layer will be exposed to the same volume of fluid.

The microfluidic cartridge 5 uses a set of standardized layers 5 in this embodiment and therefore not only make sure the layers 5 fabricated and assembled more simply and economically; but also allow layers 5 to be placed in many different combinations, such as mixing and matching of discrete, independent layers to perform complex functions of interest, rotating the position of certain layers along the axis of symmetry for different utilizations and so on. The standardized layers 5 could be sealed to one another only by the application of pressure, or using reversible double sided pressure sensitive adhesives therebetween. The standardized layers 5 obviously could apply to the layers 1,2,3,4 of the abovementioned embodiments.

Referring to FIGS. 23-26, a stacked testing assembly 500 according to a fifth embodiment of the present invention. The testing setup 20 can also assemble and test layers of a microfluidic cartridge 60. The microfluidic cartridge 60 also includes a set of standardized layers 6 stacked in the height direction, the differences is each layer 6 defining a pair of flow channels 61 connecting a pair of via ports 64*a* in one row to a pair of via ports 64*b* in the other row, therefore, a fluid sample will flow from each layer to its adjacent layer via the via ports 64*a*, 64*b* in parallel or simultaneously, the flow resistance of the fluid sample will be decreased and more layers for stacking are possible. The via ports 64*b* locate between a respective pair of fixture holes 62, while the via ports 64*a* locate outside of another pair of fixture holes 62, therefore, the via ports 64*a* form a larger space therebetween than that of the via ports 64*b*, and said two flow channels 61 extend straightly and at an acute angle.

Referring to FIGS. 27-30, a stacked testing assembly 600 according to a sixth embodiment of the present invention, each layer 7 of a microfluidic cartridge 70 defines a number of dead channels 77 locating between a pair of flow channels 71 in the longitudinal direction. Input ports 75 and output ports 76 locate at opposite ends of said dead channels 77. The dead channels 77 can be used to prevent capillary action crossover of fluid sample during flowing in said flow channels 71, air or buffer fluid can be additionally flowed through said dead channels 77 so as to carry away fluid sample which may cross over, absorbent material could also be used to line the dead channels 77.

The testing setup 20 in the present invention is capable of testing individual layers or layers in many different combinations with no change to its structure. Once test of said microfluidic cartridge is finished, covers will substitute said testing setup and be applied to said microfluidic cartridge in assembly so as to form a product for using.

It is to be understood, however, that even though numerous, characteristics and advantages of the present invention have been set fourth in the foregoing description, together with details of the structure and function of the invention, the disclosed is illustrative only, and changes may be made in detail, especially in matters of number, shape, size, and arrangement of parts within the principles of the invention to the full extent indicated by the broad general meaning of the terms in which the appended claims are expressed.

What is claimed is:

1. A microfluidic cartridge for analyzing fluid samples, comprising:

a plurality of layers stacked in a height direction; wherein each of said layers defines a standard number of via ports passing therethrough in the height direction for connecting non-adjacent layers to one another and being closed on the respective layers only if the respective layers need to receive fluid sample from said non-adjacent layers, and a standard number of alignment holes passing therethrough in the height direction and locating at corners thereof to align the layers during assembly of said layers; wherein at least one of said layers defines a standard number of input ports recessing from one side thereof in the height direction while not penetrating the other opposite side thereof, a standard number of output ports passing therethrough in the height direction and corresponding to the input ports, and flow channels connecting between the respective input ports and output ports; said fluid samples enter the layer via the input ports, flowing in the layer via the flow channels and exit of the layer via the output ports; wherein said layers includes a first layer at least includes said via ports and alignment holes, and a second layer includes said via ports, alignment holes, input ports, output ports and flow channels; said first layer stacks on an upper side of the second layer; said first layer is an electrode layer and defines a set of electrodes arranged on a lower side thereof; said second layer is a counter layer and defines flow channels on an upper side thereof, each flow channel forms a detecting region for said fluid sample passing singly, the electrodes stride across the detecting region to analyze the fluid sample; wherein the flow channels include a pair of first flow channels and a pair of second flow channels; wherein said plurality of layers further include another layer stacked on an upper side of the first layer and defining a capture chambers for capturing the selective particles from the fluid sample of interest; wherein the first layer, the second layer and said another layer are arranged with one another to allow the fluid sample of interest to sequentially pass through the pair of first flow channels in the second layer, the capture chambers in said another layer, and the pair of second flow channels in the second layer.

* * * * *